United States Patent
Unverricht et al.

(10) Patent No.: US 6,525,217 B1
(45) Date of Patent: *Feb. 25, 2003

(54) METHOD FOR THE CATALYTIC GAS-PHASE OXIDATION OF PROPENE TO ACRYLIC ACID

(75) Inventors: Signe Unverricht, Mannheim (DE); Heiko Arnold, Mannheim (DE); Andreas Tenten, Maikammer (DE); Ulrich Hammon, Mannheim (DE); Hans-Peter Neumann, Ludwigshafen (DE); Klaus Harth, Altleiningen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/914,591

(22) PCT Filed: Feb. 28, 2000

(86) PCT No.: PCT/EP00/01629

§ 371 (c)(1),
(2), (4) Date: Aug. 30, 2001

(87) PCT Pub. No.: WO00/53557

PCT Pub. Date: Sep. 14, 2000

(30) Foreign Application Priority Data

| Mar. 10, 1999 | (DE) | 199 10 508 |
| Mar. 10, 1999 | (DE) | 199 10 506 |
| Jun. 17, 1999 | (DE) | 199 27 624 |
| Oct. 7, 1999 | (DE) | 199 48 248 |
| Oct. 7, 1999 | (DE) | 199 48 241 |
| Oct. 8, 1999 | (DE) | 199 48 523 |

(51) Int. Cl.[7] .................. C07C 51/25; C07C 45/35; C07C 57/04; C07C 47/22

(52) U.S. Cl. .................. 562/544; 562/545; 562/518; 562/531; 562/532; 568/476; 568/449; 568/491

(58) Field of Search .................. 562/544, 545, 562/518, 531, 532; 568/476, 449, 491

(56) References Cited

U.S. PATENT DOCUMENTS

| 4,203,906 A | 5/1980 | Takada et al. |
| 4,298,763 A | 11/1981 | Engelbach et al. |
| 4,365,087 A | 12/1982 | Kadowaki et al. |
| 4,366,093 A | 12/1982 | Shiozaki et al. |
| 4,438,217 A | 3/1984 | Takata et al. |
| 4,537,874 A | 8/1985 | Sato et al. |
| 4,656,157 A | 4/1987 | Hofmann et al. |
| 5,364,825 A | 11/1994 | Neumann et al. |
| 5,449,821 A | 9/1995 | Neumann et al. |
| 5,677,261 A | 10/1997 | Tenten et al. |
| 5,739,391 A | 4/1998 | Ruppel et al. |
| 5,910,608 A | 6/1999 | Tenten et al. |
| 6,028,220 A | 2/2000 | Wada et al. |

FOREIGN PATENT DOCUMENTS

| DE | 25 13 405 | 10/1976 |
| DE | 28 30 765 | 1/1980 |
| DE | 30 02 829 | 7/1980 |
| DE | 31 13 179 | 1/1982 |
| DE | 33 00 044 | 7/1983 |
| DE | 33 38 380 | 4/1984 |
| DE | 44 42 346 | 5/1996 |
| DE | 198 55 913 | 6/2000 |
| EP | 0 015 565 | 9/1980 |
| EP | 0 184 790 | 6/1986 |
| EP | 0 253 409 | 1/1988 |
| EP | 0 257 565 | 3/1988 |
| EP | 0 279 374 | 8/1988 |
| EP | 0 293 224 | 11/1988 |
| EP | 0 450 596 | 10/1991 |
| EP | 0 575 897 | 12/1993 |
| EP | 0 700 893 | 3/1996 |
| EP | 0 714 700 | 6/1996 |
| EP | 0 807 465 | 11/1997 |
| WO | WO 98/24746 | 6/1998 |

Primary Examiner—Brian J. Davis
(74) Attorney, Agent, or Firm—Oblon, Spivak, McClelland, Maier & Neustadt, P.C.

(57) ABSTRACT

A process for the catalytic gas-phase oxidation of propene to acrylic acid, in which the reaction gas starting mixture is oxidized, with an increased propene loading, in a first reaction stage, over a first fixed-bed catalyst and then the acrolein-containing product gas mixture of the first reaction stage is oxidized, in a second reaction stage, with an increased acrolein loading, over a second fixed-bed catalyst, the catalyst moldings in both reaction stages having an annular geometry.

57 Claims, No Drawings

METHOD FOR THE CATALYTIC GAS-PHASE OXIDATION OF PROPENE TO ACRYLIC ACID

The present invention relates to a process for the catalytic gas-phase oxidation of propene to acrylic acid, in which a reaction gas starting mixture 1 which comprises propene, molecular oxygen and at least one inert gas and contains the molecular oxygen and the propene in a molar $O_2:C_3H_6$ ratio of $\geq 1$ is first passed, in a first reaction stage at elevated temperatures, over a first fixed-bed catalyst whose active material is at least one multimetal oxide containing molybdenum and/or tungsten and bismuth, tellurium, antimony, tin and/or copper, in such a way that the propene conversion in a single pass is $\geq 90$ mol % and the associated selectivity of the acrolein formation and of the acrylic acid byproduct formation together is $\geq 90$ mol %, the temperature of the product gas mixture leaving the first reaction stage is, if required, reduced by direct and/or indirect cooling and, if required, molecular oxygen and/or inert gas are added to the product gas mixture, and the product gas mixture, as reaction gas starting mixture 2 which comprises acrolein, molecular oxygen and at least one inert gas and contains the molecular oxygen and the acrolein in a molar $O_2:C_3H_4O$ ratio of $\geq 0.5$, is then passed, in a second reaction stage at elevated temperatures, over a second fixed-bed catalyst whose active material is at least one multimetal oxide containing molybdenum and vanadium, in such a way that the acrolein conversion in a single pass is $\geq 90$ mol % and the selectivity of the acrylic acid formation balanced over both reaction stages is $\geq 80$ mol %, based on propene converted.

The abovementioned process for the catalytic gas-phase oxidation of propene to acrylic acid is generally known (cf. for example DE-A 3002829). In particular, the two reaction stages are known per se (cf. for example EP-A 714700, EP-A 700893, EP-A 15565, DE-C 2830765, DE-C 3338380, JP-A 91/294239, EP-A 807465, WO 98/24746, EP-B 279374, DE-C 2513405, DE-A 3300044, EP-A 575897 and DE-A 19855913).

Acrylic acid is an important monomer which is used as such on its own or with alkyl esters for producing, for example, polymers suitable as adhesives.

The object of every two-stage fixed-bed gas-phase oxidation of propene to acrylic acid is in principle to achieve a very high space-time yield of acrylic acid ($STY_{AA}$) (in a continuous procedure, this is the total amount of acrylic acid, in liters, produced per hour and total volume of the catalyst bed used).

There is therefore general interest in carrying out such as two-stage fixed-bed gas-phase oxidation of propene to acrylic acid on the one hand with a very high loading of the first fixed catalyst bed with propene (which is understood as meaning the amount of propene in liters (S.T.P.) (=l (S.T.P.), the volume in liters which the corresponding amount of propene would occupy under standard temperature and pressure conditions, i.e. at 250° C. and 1 bar) which is passed as a component of the reaction gas starting mixture 1 per hour through 1 liter of catalyst bed 1) and, on the other hand, with a very high loading of the second fixed catalyst bed with acrolein (this is understood as meaning the amount of acrolein in liters (S.T.P.) (=l(S.T.P.), the volume in liters which the corresponding amount of acrolein would occupy under standard temperature and pressure conditions, i.e. at 25° C. and 1 bar) which is passed as a component of reaction mixture 2 per hour through 1 liter of catalyst bed 2) without significantly impairing the propene and acrolein conversion taking place during a single pass of the two reaction gas starting mixtures 1, 2 through the two fixed catalyst beds and the selectivity, balanced over both reaction stages, of the associated acrylic acid formation (based on propene converted).

The realization of the abovementioned is adversely affected by the fact that both the fixed-bed gas-phase oxidation of propene to acrolein and the fixed-bed gas-phase oxidation of acroleo into acrylic acid are highly exothermic on the one hand and, on the other hand, are accompanied by a variety of possible simultaneous and subsequent reactions.

In principle, the multimetal oxides suitable as catalytic active materials can be used in powder form in the fixed-bed gas-phase oxidation of propene to acrylic acid described at the outset. Usually, however, they are shaped into specific catalyst geometries before being used, since active material powder is unsuitable for industrial use owing to the poor gas permeation.

It is an object of the present invention to select the geometry of the catalyst moldings to be used in the two fixed catalyst beds of the catalytic fixed-bed gas-phase oxidation described at the outset so that, with high loading of the fixed catalyst beds with starting material and a given conversion of starting material, a very high selectivity of the desired compound acrylic acid results in a single pass through the fixed catalyst beds.

The following prior art may be used as a basis.

The conventional processes for the catalytic fixed-bed gas-phase oxidation of propene to acrolein or of acrolein to acrylic acid, wherein nitrogen is used as a main component of the inert diluent gas and moreover a fixed-bed catalyst present in the reaction zone and homogeneous along this reaction zone, i.e. having a chemically uniform composition over the fixed catalyst bed, is used and the temperature of the reaction zone is kept at a value uniform over the reaction zone (temperature of a reaction zone is understood here as meaning the temperature of the fixed catalyst bed present in the reaction zone when the process is carried out in the absence of a chemical reaction; if this temperature is not constant within the reaction zone, the term temperature of the reaction zone in this case means the number average of the (temperature of the catalyst bed along the reaction zone), limit the applicable propene or acrolein loading of the fixed catalyst bed to comparatively low values.

Thus, the propene loading used in the fixed catalyst bed is usually $\leq 155$ l (S.T.P.) of propene/l of catalyst bed·h (cf. for example EP-A 15565 (maximum propene loading=120 l (S.T.P.) of propene/l·h), DE-C 2830765 (maximum propene loading =94.5 l (S.T.P.) of propene/l·h), EP-A 804465 (maximum propene loading=128 l (S.T.P.) of propene/l·h), EP-B 279374 (maximum propene loading=112 l (S.T.P.) of propene/l·h), DE-C 2513405 (maximum propene loading= 110 l (S.T.P.) of propene/l·h), DE-A 3300044 (maximum propene loading=112 l (S.T.P.) of propene/l·h):and EP-A 575897 (maximum propene loading=120 l (S.T.P.) of propene/l·h).

Furthermore, in essentially all examples of DE-C 3338380, the maximum propene loading is 126 l (S.T.P.) of propene/l·h; only in Example 3 of this publication is a propene loading of 162 l (S.T.P.)/l·h realized, the catalyst moldings used being exclusively solid cylinders consisting of active material and having a length of 7 mm and a diameter of 5 mm.

EP-B 450596 discloses a propene loading of the catalyst bed of 202.5 l (S.T.P.) of propene/l·h, with the use of a structured catalyst bed in an otherwise conventional procedure. The catalyst moldings used are spherical coated catalysts.

EP-A 293224 likewise discloses propene loadings above 160 l (S.T.P.) of propene/l·h, an inert diluent gas completely free of molecular nitrogen being used. The catalyst geometry used is not stated.

EP-A 253409 and the associated equivalent, EP-A 257565, disclose that, when an inert diluent gas which has a higher molar heat capacity than molecular nitrogen is used, the proportion of propene in the reaction gas starting mixture can be increased. Nevertheless, in the two abovementioned publications too, the maximum realized propene loading of the catalyst bed is 140 l (S.T.P.) of propene/l·h. Neither of the two publications provides any information regarding the catalyst geometry to be used.

In a manner corresponding to the conventional processes for the catalytic fixed-bed gas-phase oxidation of propene to acrolein, the conventional processes for the catalytic fixed-bed gas-phase oxidation of acrolein to acrylic acid also usually limit the acrolein loading of the fixed catalyst bed to $\leq 150$ l (S.T.P.) of acrolein/l of catalyst·h (cf. for example EP-B 700893; the catalyst moldings used are spherical coated catalysts).

Two-stage gas-phase oxidations of propene to acrylic acid, in which the two oxidation phases are operated with both a high propene loading and a high acrolein loading of the respective fixed-bed catalyst, are virtually unknown in the prior art.

Amongst the exceptions are EP-A 253409 and the associated equivalent, EP-A 257565, cited above. Another exception is EP-A 293224 cited above, spherical coated catalysts being used in the acrolein oxidation stage.

The basic possibility of using annular geometry for the catalyst moldings to be used in the two relevant oxidation stages is known from the prior art.

For example, the ring geometry in DE-A 3113179 is suggested very generally for exothermic fixed-bed gas-phase oxidation from the point of view of "very small pressure drop". However, this publication points out that the influence of the geometry on the selectivity of product formation may differ from reaction to reaction.

Otherwise, these catalyst moldings having ring geometry for the catalytic gas-phase oxidation of propene and/or acrolein is disclosed, for example, in EP-A 575897, DE-A 19855913 and EP-A 700893. In all cases, however, the use of the catalyst moldings having ring geometry was limited to low loadings of starting material.

The present invention therefore relates to a process for the catalytic gas-phase oxidation of propene to acrylic acid, in which a reaction gas starting mixture 1 which comprises propene, molecular oxygen and at least one inert gas and contains the molecular oxygen and the propene in a molar $O_2:C_3H_6$ ratio of $\geq 1$ is first passed, in a first reaction stage at elevated temperatures, over a first fixed-bed catalyst whose active material is at least one multimetal oxide containing molybdenum and/or tungsten and bismuth, tellurium, antimony, tin and/or copper, in such a way that the propene conversion in a single pass is $\geq 90$ mol % and the associated selectivity of the acrolein formation and of the acrylic acid byproduct formation together is $\geq 90$ mol %, the temperature of the product gas mixture leaving the first reaction stage is, if required, reduced by direct and/or indirect cooling and, if required, molecular oxygen and/or inert gas are added to the product gas mixture, and the product gas mixture, as reaction gas starting mixture 2 which comprises acrolein, molecular oxygen and at least one inert gas and contains the molecular oxygen and the acrolein in a molar $O_2:C_3H_4O$ ratio of $\geq 0.5$, is then passed, in a second reaction stage at elevated temperatures, over a second fixed-bed catalyst whose active material is at least one multimetal oxide containing molybdenum and vanadium, in such a way that the acrolein conversion in a single pass is $\geq 90$ mol % and the selectivity of the acrylic acid formation balanced over both reaction stages is $\geq 80$ mol %, based on propene converted, wherein a) the loading of the first fixed-bed catalyst with the propene contained in the reaction gas starting mixture 1 is $\geq 160$ l (S.T.P.) of propene/l of catalyst bed·h, b) the loading of the second fixed-bed catalyst with the acrolein contained in the reaction gas starting mixture 2 is $\geq 140$ l (S.T.P.) of acrolein/l of catalyst bed·h and c) both the geometry of the catalyst moldings of the first fixed-bed catalyst and the geometry of the catalyst moldings of the second fixed-bed catalyst are annular, with the proviso that the external ring diameter is from 2 to 11 mm,
the ring length is from 2 to 11 mm and
the wall thickness of the ring is from 1 to 5 mm.

Annular geometries suitable according to the invention for the catalyst molding of the two fixed catalyst beds include those described in EP-A 184790, DE-A 3113179, DE-A 3300044 and EP-A 714700.

Furthermore, the annular catalyst moldings, according to the invention, of both reaction stages may be unsupported catalysts (consisting exclusively of the catalytically active multimetal oxide material), coated catalysts (an annular support has a coat of the catalytically active multimetal oxide material adsorbed onto its outer surface) or supported catalysts (an annular support contains adsorbed catalytically active multimetal oxide material).

In the novel process, annular unsupported catalysts are preferably used in the first reaction stage and annular coated catalysts in the second reaction stage. However, it is of course also possible to use the combinations "coated catalyst/unsupported catalyst" or "unsupported catalyst/unsupported catalyst" or "coated catalyst/coated catalyst" in the two successive reaction stages.

According to the invention, the preferred coated catalysts are those whose support rings have a length of from 2 to 10 mm (or from 3 to 6 mm), an external diameter of from 2 to 10 mm (or from 4 to 8 mm) and a wall thickness of from 1 to 4 mm (or from 1 to 2 mm). Very particularly preferably, the support rings measure 7 mm×3 mm×4 mm (external diameter×length×internal diameter). The thickness of the catalytically active oxide material applied as a coat to the annular support is very generally from 10 to 1000 µm, very preferably from 50 to 500 µm, particularly preferably from 100 to 500 µm, very particularly preferably from 150 to 250 µm.

The statements made above regarding the preferred geometry of the support rings of coated catalysts suitable according to the invention apply in the same way to the supported catalysts suitable according to the invention.

In the case of unsupported catalyst rings suitable according to the invention, those of which the internal diameter is from 0.1 to 0.7 times the external diameter and the length is from 0.5 to 2 times the external diameter are particularly suitable.

Advantageous unsupported catalyst rings which may be used according to the invention have an external diameter of from 2 to 10 mm (or from 3 to 7 mm), an internal diameter of at least 1.0 mm, a wall thickness of from 1 to 2 mm (or not more than 1.5 mm) and a length of from 2 to 10 mm (or from 3 to 6 mm). In the cases of unsupported catalyst rings suitable according to the invention, frequently the external diameter is from 4 to 5 mm, the internal diameter is from 1.5 to 2.5 mm, the wall thickness from 1.0 to 1.5 mm and the length from 3 to 6 mm.

This means that unsupported catalysts in the form of a hollow cylinder measure (in each case external diameter× height×internal diameter) 5 mm×3 mm×2 mm, 5 mm×2 mm×2 mm, 5 mm×3 mm×3 mm, 6 mm×3 mm×3 mm or 7 mm×3 mm×4 mm.

Suitable fixed-bed catalysts 1 for the novel process are all those whose active material is at least one Mo-, Bi- and Fe-containing multimetal oxide.

This means that in principle all those multimetal oxides which are disclosed in DE-C 3338380, DE-A 19902562, EP-A 15565, DE-C 2380765, EP-A 807465, EP-A 279374, DE-A 3300044, EP-A 575897, U.S. Pat. No. 4,438,217, DE-A 19855913, WO 98/24746, DE-A 19746210 (those of the formula II), JP-A 91/294239, EP-A 293224 and EP-A 700714 can be used as active materials for fixed-bed catalysts 1. This applies in particular to the exemplary embodiments in these publications, among which those of EP-A 15565, EP-A 575897, DE-A 19746210 and DE-A 19855913 are particularly preferred. Particularly noteworthy in this context are the multimetal oxide active material according to Example 1c of EP-A 15565 and an active material which has to be prepared in a corresponding manner but which has the composition $MO_{12}Ni_{6.5}Zn_2Fe_2Bi_1P_{0.0065}K_{0.06}O_x \cdot 10SiO_2$.

Fixed-bed catalysts suitable according to the invention which may be singled out are the example with the serial number 3 from DE-A 19855913 (stoichiometry: $Mo_{12}Co_7Fe_3Bi_{0.6}K_{0.08}Si_{1.6}O_x$) as an unsupported catalyst in the form of hollow cylinders (rings) and measuring 5 mm×3 mm×2 mm (external diameter×length×internal diameter) and the unsupported catalyst comprising multimetal oxide II according to Example 1 of DE-A 19746210. Other examples would be the annular unsupported multimetal oxide catalysts of U.S. Pat. No. 4,438,217. The latter applies in particular when these hollow cylinders measure 5 mm×2 mm×2 mm, or 5 mm×3 mm×2 mm, or 6 mm×3 mm×3 mm, or 7 mm×3 mm×4 mm (in each case external diameter×length×internal diameter).

A large number of the multimetal oxide active materials suitable for fixed-bed catalysts 1 can be subsumed under the formula I

$$Mo_{12}Bi_aFe_bX_c^1X_d^2X_e^3X_f^4O_n \qquad (I),$$

where

X¹ is nickel and/or cobalt,

X² is thallium, an alkali metal and/or an alkaline earth metal,

X³ is zinc, phosphorus, arsenic, boron, antimony, tin, cerium, lead and/or tungsten, X⁴ is silicon, aluminum, titanium and/or zirconium, a is from 0.5 to 5, b is from 0.01 to 5, preferably from 2 to 4, c is from 0 to 10, preferably from 3 to 10, d is from 0 to 2, preferably from 0.02 to 2, e is from 0 to 8, preferably from 0 to 5, f is from 0 to 10 and n is a number which is determined by the valency and frequency of the elements other than oxygen in I.

They are obtainable in a manner known per se (cf. for example DE-A 4023239) and according to the invention are, for example, either shaped as such into rings or used in the form of annular coated catalysts, i.e. inert supports preshaped into rings and coated with the active material.

In principle, active materials suitable for the fixed-bed catalysts 1, in particular active materials of the formula I, can be prepared in a simple manner by producing, from suitable sources of their elemental constituents, a very intimate, preferably finely divided, dry blend with a composition corresponding to their stoichiometry and calcining the said dry blend at from 350 to 650° C. The calcination can be carried out either under inert gas or under an oxidizing atmosphere, e.g. air (mixture of inert gas and oxygen) or under reducing atmosphere (e.g. mixture of inert gas, $NH_3$, CO and/or $H_2$). The duration of calcination may be from a few minutes to a few hours and usually decreases with temperature. Suitable sources of the elemental constituents of the multimetal oxide active materials I are those compounds which are already oxides and/or those compounds which can be converted into oxides by heating, at least in the presence of oxygen.

In addition to the oxides, suitable starting compounds of this type are in particular halides, nitrates, formates, oxalates, citrates, acetates, carbonates, amine complexes, ammonium salts and/or hydroxides (compounds such as $NH_4OH$, $(NH_4)_2CO_3$, $NH_4NO_3$, $NH_4CHO_2$, $CH_3COOH$, $NH_4CH_3CO_2$ and/or ammonium oxalate, which decompose and/or can be decomposed at the latest during the subsequent calcination to give of compounds escaping completely in gaseous form may additionally be incorporated into the intimate dry blend).

The intimate mixing of the starting compounds for the preparation of multimetal oxide materials I can be carried out in dry or in wet form. If it is effected in dry form, the starting compounds are expediently used in the form of finely divided powders and, after the mixing and any compaction, are subjected to calcination. However, the intimate mixing is preferably effected in wet form. Usually, the starting compounds are mixed with one another in the form of an aqueous solution and/or suspension. Particularly intimate dry blends are obtained in the mixing method described when exclusively dissolved sources of the elemental constituents are used as starting materials. A preferably used solvent is water. The aqueous material obtained is then dried, the drying process preferably being effected by spray drying the aqueous mixture at an outlet temperature of from 100 to 150° C.

The multimetal oxide materials suitable for novel fixed-bed catalysts 1, in particular those multimetal oxide materials of the formula I, are shaped into an annular catalyst geometry before being used for the novel process, it being possible to carry out the shaping before or after the final calcination. For example, annular unsupported catalysts can be prepared from the powder form of the active material or its uncalcined and/or partially calcined precursor material by compaction to give the desired catalyst geometry (for example by extrusion), it being possible, if required, to add assistants, e.g. graphite or stearic acid as lubricants and/or molding assistants and reinforcing agents, such as microfibers of glass, asbestos, silicon carbide or potassium titanate.

The shaping of the pulverulent active material or its pulverulent uncalcined and/or partially calcined precursor material can of course also be effected by application to inert catalyst supports preshaped into rings. The coating of the annular supports for the preparation of the coated catalysts is as a rule carried out in a suitable rotatable container, as disclosed, for example, in DE-A 2909671, EP-A 293859 or EP-A 714700. For coating the annular supports, the powder material to be applied or the support is moistened and, after application, is dried again, for example by means of hot air. The coat thickness of the powder material applied to the annular support is expediently chosen to be from 10 to 1000 μm, preferably from 50 to 500 μm, particularly preferably from 150 to 250 μm.

Suitable support materials are conventional porous or nonporous aluminas, silica, thorium dioxide, zirconium dioxide, silicon carbide or silicates, such as magnesium silicate or aluminum silicate. Supports having substantial surface roughness are preferred. This essentially nonporous, annular steatite supports having a rough surface is suitable. It is expedient to use as supports annular cylinders whose length is from 2 to 10 mm and whose external diameter is from 4 to 10 mm. Wall thickness is usually from 1 to 4 mm. Annular supports preferably to be used according to the invention have a length of from 3 to 6 mm, an external diameter of from 4 to 8 mm and a wall thickness of from 1 to 2 mm. Other supports particularly suitable according to the invention are rings measuring 7 mm×3 mm×4 mm (external diameter×length×internal diameter). The fineness of the catalytically active oxide material to be applied to the surface of the support is of course adapted to the desired coat thickness (cf. EP-A 714 700).

Alternatively, for the purpose of shaping, the annular support can also be impregnated with a solution and/or suspension containing the starting compounds of the elemental constituents of the relevant multimetal oxide material, dried and finally calcined, as described, to give supported catalysts.

Advantageous multimetal oxide active material to be used according to the invention for fixed-bed catalysts 1 are furthermore materials of the formula II

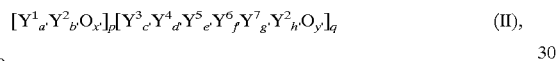  (II), where $Y^1$ is bismuth, tellurium, antimony, tin and/or copper,
$Y^2$ is molybdenum and/or tungsten,
$Y^3$ is an alkali metal, thallium and/or samarium,
$Y^4$ is an alkaline earth metal, nickel, cobalt, copper, manganese, zinc, tin, cadmium and/or mercury,
$Y^5$ is iron, chromium, cerium and/or vanadium,
$Y^6$ is phosphorus, arsenic, boron and/or antimony,
$Y^7$ is a rare earth metal, titanium, zirconium, niobium, tantalum, rhenium, ruthenium, rhodium, silver, gold, aluminum, gallium, indium, silicon, germanium, lead, thorium and/or uranium,
a' is from 0.01 to 8,
b' is from 0.1 to 30,
c' is from 0 to 4,
d' is from 0 to 20,
e' is from 0 to 20,
f' is from 0 to 6,
g' is from 0 to 15,
h' is from 8 to 16,
x' and y' are numbers which are determined by the valency and frequency of the elements other than oxygen in II
and p and q are numbers whose ratio p/q is from 0.1 to 10,
containing three-dimensional regions which are delimited from their local environment owing to their composition differing from the local environment and have the chemical composition $Y^1{}_{a'}Y^2{}_{b'}O_{x'}$ and whose maximum diameter (longest distance passing through the center of gravity of the region and connecting two points present on the surface (interface) of the region) is from 1 nm to 100 μm frequently from 10 nm to 500 nm or from 1 μm to 50 or 25 μm.

Particularly advantageous novel multimetal oxide materials II are those in which $Y^1$ is bismuth.

Preferred among these in turn are those of the formula III

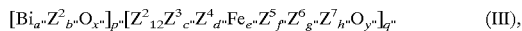  (III), where $Z^2$ is molybdenum and/or tungsten,
$Z^3$ is nickel and/or cobalt,
$Z^4$ is thallium, an alkali metal and/or an alkaline earth metal,
$Z^5$ is phosphorus, arsenic, boron, antimony, tin, cerium and/or lead,
$Z^6$ is silicon, aluminum, titanium and/or zirconium,
$Z^7$ is copper, silver and/or gold,
a" is from 0.1 to 1,
b" is from 0.2 to 2,
c" is from 3 to 10,
d" is from 0.02 to 2,
e" is from 0.01 to 5, preferably from 0.1 to 3,
f" is from 0 to 5,
g" is from 0 to 10,
h" is from 0 to 1,
x" and y" are numbers which are determined by the valency and frequency of the elements other than oxygen in III and
p" and q" are numbers whose ratio p"/q" is from 0.1 to 5, preferably from 0.5 to 2,
very particularly preferred materials III being those in which $Z^2{}_{b"}$ is (tungsten)$_{b"}$ and $Z^2{}_{12}$ is (molybdenum)$_{12}$.

It is also advantageous if at least 25 mol % (preferably at least 50 mol %, very preferably at least 100 mol %) of the total amount $[Y^1{}_{a'}Y^2{}_{b'}O_{x'}]_p$ ($[Bi_{a"}Z^2{}_{b"}O_{x"}]_{p"}$) of the multimetal oxide materials II (multimetal oxide materials III) suitable according to the invention as fixed-bed catalysts 1 are present in the multimetal oxide materials II (multimetal oxide materials III) suitable according to the invention in the form of three-dimensional regions which are delimited from their local environment owing to their chemical composition differing from their local environment and have the chemical composition $Y^1{}_{a'}Y^2{}_{b'}O_{x'}$, $[Bi_{a"}Z^2{}_{b"}O_{x"}]$ and whose maximum diameter is from 1 nm to 100 μm.

Regarding the shaping, the statements made in connection with the catalysts comprising multimetal oxide materials I are applicable regarding catalysts comprising multimetal oxide materials II.

The preparation of active material comprising multimetal oxide materials II is described, for example, in EP-A 575897 and DE-A 19855913.

Usually, the first reaction stage of the novel process is carried out in a tube-bundle reactor loaded with the annular catalysts, as described, for example, in EP-A 700714.

In the simplest manner, this means that the fixed-bed catalyst 1 to be used according to the invention is present in the metal tubes of a tube-bundle reactor, and a thermostating medium (one-zone operation), as a rule a salt melt, is passed around the metal tubes. Salt melt and reaction gas mixture can be fed in cocurrent or countercurrent in a simple manner. The salt melt (the thermostatic medium) can however be fed in a meandering manner around the tube bundles, considered over the reactor, so that, only when considered over the entire reactor is there a cocurrent or countercurrent stream with respect to the direction of flow of the reaction gas mixture. The flow velocity of the thermostating medium (heat exchange medium) is usually set such that the temperature increase (due to the exothermic nature of the reaction) of the heat exchange medium from the point of entry into the reactor to the point of exit from the reactor is from $\geq 0$ to 10° C., frequently from a 2 to 8° C., or from $\geq 3$ to 6° C. The temperature of the heat exchange medium on entering the tube-bundle reactor is as a rule from 310 to 360° C., frequently from 320 to 340° C.

Particularly suitable heat exchange media are fluid thermostatic media. The use of melts of salts, such as potassium nitrate, potassium nitrite, sodium nitrite and/or sodium nitrate, or of metals having a low melting point, such as sodium, mercury and alloys of various metals, is particularly advantageous.

The reaction gas starting mixture 1 of the catalyst bed 1 is expediently preheated to the reaction temperature before being fed in. In the novel variant of the first reaction stage described above, this is frequently from 310 to 360° C., often from 320 to 340° C.

In a manner expedient with regard to application technology, the first reaction stage of the novel process is carried out in a two-zone tube-bundle reactor. A preferred variant of a two-zone tube-bundle reactor which may be used according to the invention is disclosed in DE-C 2830765. However, the two-zone tube-bundle reactors disclosed in DE-C 2513405, U.S. Pat. No. 3,147,084, DE-A 2201528, EP-A 383224 and DE-A 2903218 are also suitable for carrying out the first reaction stage of the novel process.

In the simplest manner, this means that the fixed-bed catalyst 1 to be used according to the invention is present in the metal tubes of a tube-bundle reactor, and two thermostatic media essentially spatially separated from one another, as a rule salt melts, are passed around the metal tubes. According to the invention, the tube section over which the respective salt bath extends represents a reaction zone. In the simplest manner, this means that a salt bath A flows around that section of the tubes (the reaction zone A) in which the oxidative reaction of the propene (in the single pass) takes place until a conversion of from 40 to 80 mol % is achieved and a salt bath B flows round that section of the tubes (the reaction zones B) in which the subsequent oxidative reaction of the propene (in a single pass) takes place until a conversion of at least 90 mol % is reached (if required, the reaction zones A, B to be used according to the invention may be followed by further reaction zones which are kept at individual temperatures).

In terms of application technology, the first reaction stage of the novel process expediently comprises no further reaction zones, i.e. the salt bath B expediently flows around that section of the tubes in which the subsequent oxidative reaction of the propene (in a single pass) takes place until conversion of $\geq 92$ mol % or $\geq 94$ mol % or more is reached.

Usually, the beginning of reaction zone B is behind the hot-spot maximum of reaction zone A. The hot-spot maximum of reaction zone B is usually below the hot-spot maximum temperature of reaction zone A.

According to the invention, the two salt baths A, B can be passed cocurrent or countercurrent through the space surrounding the reaction tubes, relative to the direction of flow of the reaction gas mixture flowing through the reaction tubes. According to the invention, cocurrent flow can of course also be used in reaction zone A, and countercurrent flow in the reaction zone B (or vice versa).

In all the abovementioned configurations, within the respective reaction zone, a transverse flow can also be superposed on the flow of the salt melt parallel to the reaction tubes, so that the individual reaction zone corresponds to a tube-bundle reactor as described in EP-A 700714 or in EP-A 700893 and, in longitudinal section overall, a meandering flow of the exchange medium results through the catalyst tube bundle.

The reaction gas starting mixture 1 of the catalyst bed 1 is expediently preheated to the reaction temperature before being fed in.

In the abovementioned tube-bundle reactors (this also applies to the one-zone tube-bundle reactors), the catalyst tubes are usually made of ferritic steel and typically have a wall thickness of from 1 to 3 mm. The internal diameter is as a rule from 20 to 30 mm, frequently from 21 to 26 mm. In terms of application technology, the number of catalyst tubes housed in the tube-bundle container is expediently at least 5000, preferably at least 10,000. Frequently, the number of catalyst tubes housed in the reaction container is from 15,000 to 30,000. Tube-bundle reactors having more than 40,000 catalyst tubes tend to be the exception. Within the container, the catalyst tubes are usually homogeneously distributed, the distribution expediently being chosen so that the distance between the central inner axes or adjacent catalyst tubes (i.e. the catalyst tube spacing) is from 35 to 45 mm (cf. for example EP-B 468290).

Particularly suitable heat exchange media are fluid thermostatic media. The use of melts of salts, such as potassium nitrate, potassium nitrite, sodium nitrite and/or sodium nitrate, or of metals having a low melting point, such as sodium, mercury and alloys of various metals, is particularly advantageous.

As a rule, in all abovementioned configurations of the flow in the two-zone tube-bundle reactors, the flow velocity within the two required circulations of heat exchange media is chosen so that the temperature of the heat exchange medium increases from the point of entry into the reaction zone to the point of exit from the reaction zone (due to the exothermic nature of the reaction) by from 0 to 15° C., i.e. according to the invention the abovementioned $\Delta T$ may be from 1 to 10° C. or from 2 to 8° C. or from 3 to 6° C.

According to the invention, the temperature of the heat exchange medium on entering reaction zone A is usually from 310 to 340° C. According to the invention, the temperature of the heat exchange medium on entering reaction zone B is usually on the one hand from 315 to 380° C. and, on the other hand, simultaneously at least 5° C. above the temperature of the heat exchange medium on entering reaction zone A.

Preferably, the temperature of the heat exchange medium on entering reaction zone B is at least 10° C. above the temperature of the heat exchange medium entering reaction zone A. The difference between the temperatures on entering reaction zones A and B may thus be, according to the invention, up to 20° C., up to 25° C., up to 30° C., up to 40° C., up to 45° C. or up to 50° C. Usually, the abovementioned temperature difference will however not be more than 50° C. The higher the chosen propene loading of the catalyst bed 1 in the novel process, the greater should be the difference between the temperature of the heat exchange medium on entering the reaction zone A and the temperature of the heat exchange medium on entering the reaction zone B.

According to the invention, the temperature of the heat exchange medium on entering the reaction zone B is advantageously from 330 to 370° C. and particularly advantageously from 340 to 370° C.

In the novel process, the two reaction zones A, B can of course also be realized in tube-bundle reactors spatially separated from one another. If required, a heat exchanger may also be mounted between the two reaction zones A, B. Of course, the two reaction zones A, B can also be designed as a fluidized bed.

Furthermore, in the novel process (both in the 1-zone and in the 2-zone variant), it is also possible to use catalyst beds 1 whose volume-specific activity increases continuously, abruptly or stepwise in the direction of flow of the reaction gas starting mixture 1 (this may be effected, for example, as described in WO 98/24746 or as described in JP-A 91/294239 or by using inert material as diluent). In addition to nitrogen, steam and/or oxides of carbon, it is also possible to use the inert diluent gases recommended in EP-A 293224 and in EP-B 257565 (for example, only propane or only methane, etc.). The latter may, if required, also be used in combination with a volume-specific activity of the catalyst bed which increases in the direction of flow of the reaction gas mixture.

It should also once again be pointed out here that in particular the two-zone tube-bundle reactor type described in German published application DE-B 2,201,528 may be used for carrying out reaction stage 1 of the novel process, said reactor type providing the possibility of transferring a portion of the relatively hot heat transfer medium of reaction zone B to reaction zone A in order, if required, to heat up a cold reaction gas starting mixture or a cold recycle gas. Furthermore, the tube-bundle characteristic within an individual reaction zone can be designed as described in EP-A 382098.

According to the invention, it has proven expedient to cool the product gas mixture leaving the first reaction zone before entry into the second reaction stage, in order thus to suppress subsequent complete combustion of parts of the acrolein formed in the first reaction stage. For this purpose, an aftercooler is usually connected between the two reaction stages. In the simplest case, this may be an indirect tube-bundle heat exchanger. The product gas mixture is as a rule passed through the tubes and the heat exchange medium whose type may correspond to the heat exchange media recommended for the tube-bundle reactors is fed around the tubes. Advantageously, the interior of the tubes is filled with inert backings (e.g. stainless steel spirals, steatite rings, steatite balls, etc.). These improve the heat exchange and trap any molybdenum trioxide subliming from the fixed catalyst bed of the first reaction stage, before entry of said molybdenum trioxide into the second reaction stage. It is advantageous if the aftercooler is made of stainless steel coated with zinc silicate coating material.

As a rule, the propene conversion in the first reaction stage in the novel process is $\geq 92$ mol % or a 94 mol %, based on a single pass. The selectivity of the acrolein formation and of the acrylic acid byproduct formation resulting in a single pass in the first reaction stage is as a rule $\geq 92$ mol % or $\geq 94$ mol % or frequently $\geq 95$ mol % or $\geq 96$ mol % or $\geq 97$ mol %.

The novel process is suitable for propene loadings of the catalyst bed 1 of $\geq 165$ l (S.T.P.)/l·h or $\geq 170$ l (S.T.P.)/l·h or $\geq 175$ l (S.T.P.)/l·h or $\geq 180$ l (S.T.P.)/l·h, but also for propene loadings of the catalyst bed 1 of $\geq 185$ l (S.T.P.)/l·h or $\geq 190$ l (S.T.P.)/l·h or $\geq 200$ l (S.T.P.)/l·h or $\geq 210$ l (S.T.P.)/l·h and for loadings of $\geq 220$ l (S.T.P.)/l·h or $>230$ l (S.T.P.)/l·h or a 240 l (S.T.P.)/l·h or $\geq 250$ l (S.T.P.)/l·h.

The inert gas to be used according to the invention for the reaction gas starting mixture 1 may comprise $\geq 20$ or $\geq 30$ or $\geq 40$ or $\geq 50$ or $\geq 60$ or $\geq 70$ or $\geq 80$ or $\geq 90$ or $\geq 95$% by volume of molecular nitrogen.

In the case of propene loadings of the catalyst bed 1 above 250 l (S.T.P.)/l·h, the presence of inert diluent gases (here, inert diluent gases generally mean those which undergo less than 5%, preferably less than 2%, conversion during a single pass through the respective reaction stage) such as propane, ethane, methane, pentane, butane, $CO_2$, CO, steam and/or noble gases, is recommended for the reaction gas starting mixture 1 for the novel process. However, these gases and their mixtures may also be present at lower novel propene loadings of the catalyst bed 1 in the reaction gas starting mixture 1 or may be used as sole diluent gases. It is surprising that the novel process can generally also be carried out with good selectivities in the case of homogeneous, i.e. chemically uniform, catalyst bed 1.

With increasing propene loading, the two-zone procedure described is preferred compared with the one-zone procedure described in the first reaction stage.

In the normal process according to the invention, the propene loading of the first fixed-bed catalyst usually does not exceed 600 l (S.T.P.)/l·h. Typically, the propene loadings of the first fixed-bed catalyst in the novel process are $\leq 300$ l (S.T.P.)/l·h, frequently $\leq 250$ l (S.T.P.)/l·h.

In the novel process, the operating pressure in the first reaction stage may be either below atmospheric pressure (e.g. up to 0.5 bar) or above atmospheric pressure. Typically, the operating pressure in the first reaction stage is from 1 to 5, frequently from 1.5 to 3.5, bar. Usually, the reaction pressure in the first reaction stage does not exceed 100 bar.

The molar $O_2:C_3H_6$ in the reaction gas starting mixture 1 must be, according to the invention, $\geq 1$. Usually, this ratio is $\leq 3$. Frequently, the molar $O_2:C_3H_6$ ratio and the reaction gas starting mixture 1 is, according to the invention, $\geq 1.5$ and $\leq 2.0$.

Suitable sources of the molecular oxygen required in the first reaction stage are both air and air depleted in molecular nitrogen (e.g. $\geq 90$% by volume of $O_2$, $\leq 10$% by volume of $N_2$).

According to the invention, the propene fraction of the reaction gas starting mixture 1 may be, for example, from 4 to 15, frequently from 5 to 12, % by volume or from 5 to 8% by volume (based in each case on the total volume).

The novel process is frequently carried out at a volume ratio of propene to oxygen to inert gases (including steam) in the reaction gas starting mixture 1 of 1:(1.0 to 3.0):(5 to 25), preferably 1:(1.5 to 2.3):(10 to 15).

Apart from said components, as a rule the reaction gas starting mixture 1 contains essentially no further components.

In terms of application technology, the product gas mixture of the first reaction stage is expediently cooled, in the abovementioned aftercooler, to a temperature of from 210 to 290° C., frequently from 220 to 260° C. or from 225 to 245° C. It is entirely possible to cool the product gas mixture of the first reaction stage to temperatures which are below the temperature of the second reaction stage. However, the aftercooling described is by no means compulsory and can be dispensed with as a rule in particular if the path of the product gas mixture from the first reaction stage to the second reaction stage is kept short. Usually, the novel process is furthermore realized in such a way that the oxygen demand in the second reaction stage is not covered by a correspondingly high oxygen content of the reaction gas starting mixture 1, but the required oxygen is added in the region between the first and second reaction stage. This can be effected before, during and/or after the aftercooling. Suitable sources of the molecular oxygen required in the second reaction stage of both pure oxygen and mixtures of oxygen and inert gas, e.g. air or air depleted in molecular nitrogen (e.g. $\geq 90$% by volume of $O_2$, $\leq 10$% by volume of $N_2$). The oxygen source is added regularly in a form compressed to the reaction pressure.

According to the invention, the acrolein fraction of the reaction gas starting mixture 2 thus produced may be, for example, from 3 to 15, frequently from 4 to 10, % by volume or from 5 to 8% by volume (based in each case on the total volume).

According to the invention, the molar $O_2$:acrolein ratio in the reaction gas starting mixture 2 must be $\geq 0.5$ or 1. Usually, this ratio is $\leq 3$. Frequently, the molar $O_2$:acrolein ratio and the reaction gas starting mixture 2 is, according to the invention, from 1 to 2 or from 1 to 1.5. Frequently, the novel process is carried out with a volume ratio (1 (S.T.P.)) of acrolein to oxygen to steam to inert gas in the reaction gas starting mixture 2 of 1:(0.5 or 1 to 3):(0 to 20):(3 to 30), preferably of 1:(1 to 3):(0.5 to 10):(7 to 10).

The operating pressure in the second reaction stage may be either below atmospheric pressure (for example up to 0.5 bar) or above atmospheric pressure. Typically, the operating pressure in the second reaction zone is, according to the invention, from 1 to 5, frequently from 1 to 3, bar. Usually, the reaction pressure in the second reaction zone does not exceed 100 bar.

Like the first reaction stage, the second reaction stage of the novel process can be carried out in a simple manner in a tube-bundle reactor loaded with annular catalysts and as described, for example, in EP-A 700893.

In the simplest manner, this means that the fixed-bed catalyst 2 to be used according to the invention is present in the metal tubes of a tube-bundle reactor, and a thermostatic medium (one-zone procedure), as a rule a salt melt, is passed around the metal tubes. Salt melt and reaction gas mixture may be fed cocurrent or countercurrent in a simple manner. The thermostatic medium can, however, also be passed in a meandering manner around the tube bundle, considered over the reactor, so that, considered only over the entire reactor, there is cocurrent or countercurrent flow with respect to the direction of flow of the reaction gas mixture. The volume flow rate of the thermostatic medium (heat exchange medium) is usually such that the temperature increase (due to the exothermic nature of the reaction) of the heat exchange medium from the point of entry into the reactor to the point of exit from the reactor is from $\geq 0$ to $10°$ C., frequently from $\geq 2$ to $8°$ C. or from $\geq 3$ to $6°$ C. The temperature of the heat exchange medium on entry in the tube-bundle reactor is as a rule from 230 to $300°$ C., frequently from 245 to $285°$ C. or from 245 to $265°$ C. Suitable heat exchange media are the fluid thermostatic media that have been described above for the first reaction stage.

Expediently, the reaction gas starting mixture 2 of the catalyst bed 2 is preheated to the reaction temperature before being fed in. In the novel variant of the second reaction stage described above, this is frequently from 230 to $300°$ C., often from 245 to $285°$ C. or from 245 to $265°$ C.

As a rule, a one-zone procedure of the first reaction stage is combined with a one-zone procedure of the second reaction stage, the relative flow of the reaction gas mixture and thermostatic medium being chosen to be identical in the two stages.

However, the second reaction stage of the novel process can of course also be realized, in a manner corresponding to the first reaction stage, as two spatially successive reaction zones C, D, the temperature of the reaction zone C expediently being from 230 to $270°$ C. and the temperature of the reaction zone D from 250 to $300°$ C. and at the same time at least $10°$ C. above the temperature of the reaction zone C.

The reaction zone C preferably extends to an acrolein conversion of from 65 to 80 mol %. Moreover, the temperature of the reaction zone C is advantageously from 245 to $260°$ C. The temperature of the reaction zone D is preferably at least $20°$ C. above the temperature of the reaction zone C and is advantageously from 265 to $285°$ C.

The higher the chosen acrolein loading of the catalyst bed 2 in the novel process, the greater should be the chosen difference between the temperature of the reaction zone C and the temperature of the reaction zone D. Usually, however, the abovementioned temperature difference in the novel process is not more than $40°$ C., i.e. the difference between the temperature of the reaction zone C and that of the reaction zone D may be, according to the invention, up to $15°$ C., up to $25°$ C., up to $30°$ C., up to $35°$ C. or up to $40°$ C.

In the novel process, the acrolein conversion in the novel process may be in general $\geq 92$ or $\geq 94$ or $\geq 96$ or $\geq 98$ and frequently even $\geq 99$ mol %, based on a single pass of the second reaction stage. The selectivity of the acrylic acid formation may be, as a rule, $\geq 92$ or $\geq 94$ mol %, frequently $\geq 95$ or $\geq 96$ or $\geq 97$ mol %, based on acrolein converted.

The novel process is suitable for acrolein loadings of the catalyst bed 2 of $\geq 140$ l (S.T.P.)/l·h or $\geq 150$ l (S.T.P.)/l·h or $\geq 160$ l (S.T.P.)/l·h or $\geq 170$ l (S.T.P.)/l·h or $\geq 175$ l (S.T.P.)/l·h or $\geq 180$ l (S.T.P.)/l·h, but also for acrolein loadings of the catalyst bed 2 of $\geq 185$ l (S.T.P.)/l·h or $\geq 190$ l (S.T.P.)/l·h or $\geq 200$ l (S.T.P.)/l·h or $\geq 210$ l (S.T.P.)/l·h and for loadings of $\geq 220$ l (S.T.P.)/l·h or >230 l (S.T.P.)/l·h or 240 l (S.T.P.)/l·h or $\geq 250$ l (S.T.P.)/l·h.

The inert gas concomitantly to be used according to the invention in the second reaction stage may comprise $\geq 30$ or $\geq 40$ or $\geq 50$ or $\geq 60$ or $\geq 70$ or $\geq 80$ or $\geq 90$ or $\geq 95\%$ by volume of molecular nitrogen.

Expediently, the inert diluent gas in the second reaction stage in the novel process comprises from 5 to 20% by weight of $H_2O$ (formed in the first reaction stage) and from 70 to 90% by weight of $N_2$.

Apart from the components stated in this publication, the reaction gas starting mixture 2 usually contains essentially no further components.

In the case of acrolein loadings of the second fixed-bed catalyst above 250 l (S.T.P.)/l·h, the presence of inert diluent gases, such as propane, ethane, methane, butane, pentane, $CO_2$, CO, steam and/or noble gases, is recommended for the reaction gas starting mixture 2. However, these gases can of course also be present at lower acrolein loadings. The novel process can generally be carried out with good selectivity using a homogeneous, i.e. chemically uniform, catalyst bed 2.

In the novel process, the acrolein loading of the second fixed-bed catalyst usually does not exceed 600 l (S.T.P.)/l·h. Typically, the acrolein loadings of the catalyst bed 2 in the novel process are $\leq 300$ l (S.T.P.)/l·h, frequently $\leq 250$ l (S.T.P.)/l·h, without a significant decline in conversion and selectivity.

As a rule, the acrolein loading of the second catalyst bed in the novel process is about 10 l (S.T.P.)/l·h, frequently about 20 or 25 l (S.T.P.)/l·h, below the propene loading of the first catalyst bed. This is primarily due to the fact that, in the first reaction stage, both conversion and selectivity with respect to acrolein do not as a rule reach 100%. Furthermore, the oxygen demand of the second reaction stage is usually covered by air. With increasing acrolein loading, the two-zone procedure described is preferred compared with the one-zone procedure carried out in the second reaction stage.

It is noteworthy that, in the novel process, the selectivity of the acrylic acid formation, balanced over both reaction stages and based on propene converted, may be as a rule $\geq 83$ mol %, frequently $\geq 85$ mol % or $\geq 88$ mol %, often $\geq 90$ mol % or 93 mol %, even at the highest propene and acrolein loadings.

Annular fixed-bed catalysts 2 to be used according to the invention which are suitable for the gas-phase catalytic acrolein oxidation in the second reaction stage are all those whose active material is at least one Mo- and V-containing multimetal oxide.

Such suitable multimetal oxide active materials are described in, for example, U.S. Pat. No. 3,775,474, U.S. Pat. No. 3,954,855, U.S. Pat. No. 3,893,951 and U.S. Pat. No. 4,339,355. Also particularly suitable are the multimetal oxide active materials of EP-A 427 508, DE-A 2 909 671, DE-C 31 51 805, German published application DE-B 2,626,887, DE-A 43 02 991, EP-A 700 893, EP-A 714 700 and DE-A 19 73 6105. Particularly preferred in this context are the exemplary embodiments of EP-A 714 700 and DE-A 19 73 6105.

A large number of the multimetal oxide active materials suitable for fixed-bed catalysts 2 can be subsumed under the formula IV $$Mo_{12}V_aX^1_bX^2_cX^3_dX^4_eX^5_fX^6_gO_n \quad (IV),$$

where:

$X^1$ is W, Nb, Ta, Cr and/or Ce,
$X^2$ is Cu, Ni, Co, Fe, Mn and/or Zn,
$X^3$ is Sb and/or Bi,
$X^4$ is one or more alkali metals,
$X^5$ is one or more alkaline earth metals,
$X^6$ is Si, Al, Ti and/or Zr,
a is from 1 to 6,
b is from 0.2 to 4,
c is from 0.5 to 18,
d is from 0 to 40,
e is from 0 to 2,
f is from 0 to 4,
g is from 0 to 40 and
n is a number which is determined by the valency and frequency of the elements other than oxygen in IV.

Preferred embodiments of the active multimetal oxides IV are those of the formula IV where $X^1$ is W, Nb, and/or Cr,
$X^2$ is Cu, Ni, Co and/or Fe,
$X^3$ is Sb,
$X^4$ is Na and/or K,
$X^5$ is Ca, Sr and/or Ba,
$X^6$ is Si, Al and/or Ti,
a is from 1.5 to 5,
b is from 0.5 to 2,
c is from 0.5 to 3,
d is from 0 to 2,
e is from 0 to 0.2,
f is from 0 to 1 and
n is a number which is determined by the valency and frequency of the elements other than oxygen in IV.

Very particularly preferred multimetal oxides IV are however those of the formula V $$Mo_{12}V_{a'}Y^1_{b'}Y^2_{c'}Y^5_{f'}Y^6_{g'}O_{n'} \quad (V)$$

where $Y^1$ is W and/or Nb,
$Y^2$ is Cu and/or Ni,
$Y^5$ is Ca and/or Sr,
$Y^6$ is Si and/or Al,
a' is from 2 to 4,
b' is from 1 to 1.5,
c' is from 1 to 3,
f' is from 0 to 0.5,
g' is from 0 to 8 and
n' is a number which is determined by the valency and frequency of the elements other than oxygen in V.

The multimetal oxide active materials (IV) suitable according to the invention are obtainable in a manner known per se, for example disclosed in DE-A 4335973 or in EP-A 714700.

In principle, multimetal oxide active materials suitable according to the invention for fixed-bed catalysts 2, in particular those active materials of the formula IV, can be prepared in a simple manner by producing, from suitable sources of elemental constituents thereof, a very intimate, preferably finely divided, dry blend having a composition corresponding to their stoichiometry and calcining said dry blend at from 350 to 600° C. The calcination may be carried out either under inert gas or under an oxidizing atmosphere, e.g. air (mixture of inert gas and oxygen) or under a reducing atmosphere (e.g. mixture of inert gas and reducing gases, such as $H_2$, $NH_3$, CO, methane and/or acrolein or said reducing gases by themselves). The duration of calcination may be from a few minutes to a few hours and usually decreases with increasing temperature. Suitable sources of the elemental constituents of the multimetal oxide active materials (IV are those compounds which are already oxides and/or those compounds which can be converted into oxides by heating, at least in the presence of oxygen.

The intimate mixing of the starting compounds for the preparation of multimetal oxide materials IV can be carried out in dry or in wet form. If it is effected in dry form, the starting compounds are expediently used in the form of finely divided powder and, after mixing and any compaction, are subjected to calcination. The intimate mixing is however preferably carried out in wet form.

Usually, the starting compounds are mixed with one another in the form of an aqueous solution and/or suspension. Particular intimate dry blends are obtained in the mixing process described when exclusively dissolved sources of the elemental constituents are used as starting materials. A preferably used solvent is water. The aqueous material obtained is then dried, the drying process preferably being carried out by spray drying the aqueous mixture at outlet temperatures of from 100 to 150° C.

The multimetal oxide materials suitable for fixed-bed catalysts 2, in particular the multimetal oxide materials of the formula IV, are used for the novel process after shaping to give annular catalyst geometries, it being possible to carry out the shaping before or after the final calcination, in a manner particularly corresponding to that in the case of fixed-bed catalysts 1. For example, annular unsupported catalysts can be prepared completely analogously from the powder form of the active material or its uncalcined precursor material by compaction to give the desired catalyst geometry (for example by extrusion), it being possible, if required, to add assistants, e.g. graphite or stearic acid as lubricants and/or molding assistants and reinforcing agents, such as microfibers of glass, asbestos, silicon carbide or potassium titanate. Suitable unsupported catalyst geometries, as stated above, are hollow cylinders having an external diameter and a length of from 2 to 10 mm. A wall thickness of from 1 to 3 mm is expedient.

Of course, the shaping of the pulverulent active material or its pulverulent uncalcined precursor material can also be carried out by application to inert catalyst supports preshaped into rings. The coating of the supports for the preparation of the coated catalysts is carried out as a rule in a suitable rotatable container, as disclosed, for example, in DE-A 2909671, EP-A 293859 or EP-A 714700.

For coating the supports, the powder material to be applied is expediently moistened and, after the application, is dried again, for example by means of hot air. The coat thickness of the powder material applied to the support is expediently chosen to be from 10 to 1000 μm, preferably from 50 to 500 μm, particularly preferably from 150 to 250 μm.

Suitable support materials are conventional porous or nonporous aluminas, silica, thorium dioxide, zirconium dioxide, silicon carbide or silicates, such as magnesium silicate or aluminum silicate. The supports having substantial surface roughness are preferred. It is suitable to use as supports hollow cylinders whose length is from 2 to 10 mm and whose external diameter is from 4 to 10 mm. The wall thickness is moreover usually from 1 to 4 mm. Annular supports preferably to be used according to the invention have a length of from 3 to 6 mm, an external diameter of from 4 to 8 mm and a wall thickness of from 1 to 2 mm. According to the invention, rings measuring 7 mm×3 mm×4 mm (external diameter×length×internal diameter) are also particularly suitable as supports. The fineness of the catalytically active oxide materials to be applied to the surface of the support is of course tailored to the desired coat thickness (cf. EP-A 714 700).

Of course, the multimetal oxide active material of the fixed-bed catalysts 2 can also be shaped into annular supported catalysts.

Advantageous multimetal oxide active materials to be used according to the invention as fixed-bed catalysts 2 are furthermore materials of the formula VI $$[D]_p[E]_q \quad (VI),$$

where

D is $Mo_{12}V_{a''}Z^1_{b''}Z^2_{c''}Z^3_{d''}Z^4_{e''}Z^5_{f''}Z^6_{g''}O_{x''}$,

E is $Z^7_{12}Cu_{h''}H_{i''}O_{y''}$, $Z^1$ is W, Nb, Ta, Cr and/or Ce, $Z^2$ is Cu, Ni, Co, Fe, Mn and/or Zn, $Z^3$ is Sb and/or Bi, $Z^4$ is Li, Na, K, Rb, Cs and/or H, $Z^5$ is Mg, Ca, Sr and/or Ba, $Z^6$ is Si, Al, Ti and/or Zr, $Z^7$ is Mo, W, V, Nb and/or Ta, a" is from 1 to 8, b" is from 0.2 to 5, c" is from 0 to 23, d" is from 0 to 50, e" is from 0 to 2, f" is from 0 to 5, g" is from 0 to 50, h" is from 4 to 30, i" is from 0 to 20 and x" and y" are numbers which are determined by the valency and frequency of the elements other than oxygen in VI and p and q are numbers other than zero, whose ratio p/q is from 160:1 to 1:1, which are obtainable by separately preforming a multimetal oxide material E $$Z^7_{12}Cu_{h''}H_{i''}O_{y''} \quad (E),$$

in finely divided form (starting material 1) and then incorporating the preformed solid starting material 1 into an aqueous solution, an aqueous suspension or a finely divided dry blend of sources of the elements Mo, V, $Z^1$, $Z^2$, $Z^3$, $Z^4$, $Z^5$ and $Z^6$, which contains the abovementioned elements in the stoichiometry D $$Mo_{12}V_{a''}Z^1_{b''}Z^2_{c''}Z^3_{d''}Z^4_{e''}Z^5_{f''}Z^6_{g''} \quad (D),$$

(starting material 2), in the desired ratio p:q, if required drying the resulting aqueous mixture, and calcining the dry precursor material thus obtained, at from 250 to 600° C., before or after it is shaped to give the desired catalyst geometry.

The multimetal oxide materials VI where the preformed solid starting material 1 is incorporated into an aqueous starting material 2 at ≦70° C. are preferred. A detailed description of the preparation of active materials comprising multimetal oxide VI is contained, for example, in EP-A 668104, DE-A 19736105 and DE-A 19528646.

Regarding the shaping, the statements made in the case of the active materials comprising multimetal oxide IV are applicable for active materials comprising multimetal oxide VI.

In a manner expedient for application technology, the second reaction stage of the novel process is carried out in a two-zone tube-bundle reactor. A preferred variant of a two-zone tube-bundle reactor which may be used according to the invention for the second reaction stage is disclosed in DE-C 2830765. However, the two-zone tube-bundle reactors disclosed in DE-C 2513405, U.S. Pat. No. 3,147,084, DE-A 2201528, EP-A 383224 and DE-A 2903582 are also suitable for carrying out the second reaction stage of the novel process.

In a simple manner, this means that the fixed-bed catalyst to be used according to the invention is present in the metal tubes of a tube-bundle reactor, and two thermostating media essentially spatially separated from one another, as a rule salt melts, are passed around the metal tubes. The tube section over which the respective salt bath extends represents, according to the invention, a reaction zone.

In a simple manner, this means that a salt bath C flows around those sections of the tubes (the reaction zone C) in which the oxidative reaction of the acrolein (in a single bath) takes place until a conversion of from 55 to 85 mol % is reached, and a salt bath D flows round that section of the tubes (reaction zone D) in which the subsequent oxidative reaction of the acrolein (in a single pass) takes place until a conversion of at least 90 mol % is reached (if required, the reaction zones C, D to be used according to the invention may be followed by further reaction zones which are kept at individual temperatures).

It is expedient in terms of application technology if the reaction stage 2 of the novel process comprises no further reaction zones, i.e. the salt bath D expediently flows around that section of the tubes in which the subsequent oxidative reaction of the acrolein (in a single pass) takes place to a conversion of ≧92 mol % or t 94 mol % or ≧96 mol % or ≧98 mol %, and frequently even ≧99 mol % or more.

Usually, the beginning of the reaction zone D is behind the hot-spot maximum of the reaction zone C. The temperature of the hot-spot maximum of the reaction zone D is usually below the hot-spot maximum temperature of the reaction zone C.

The two salt baths C, D can, according to the invention, be passed cocurrent or countercurrent through the space surrounding the reaction tubes, relative to the direction of flow of the reaction gas mixture flowing through the reaction tubes. According to the invention, cocurrent flow can of course also be used in the reaction zone C, and countercurrent flow in the reaction zone D (or vice versa).

In all the abovementioned configurations within the respective reaction zone, a transverse flow can also be superposed on the flow of the salt melt parallel to the reaction tubes, so that the individual reaction zone corresponds to a tube-bundle reactor as described in EP-A 700714 or in EP-A 700893 and, over the longitudinal section as a whole a meandering flow of the heat exchange medium results through the catalyst tube bundle.

In the abovementioned tube-bundle reactors (as in the tube-bundle reactors of the one-zone procedure), the catalyst tubes used are usually made of ferritic steel and typically have a wall thickness of from 1 to 3 mm. Their internal diameter is as a rule from 20 to 30 mm, frequently from 22 to 26 mm. In terms of application technology, the number of catalyst tube housed in the tube-bundle container is expediently at least 5000, preferably at least 10,000. Frequently, the number of catalyst tubes housed in the reaction container is from 15,000 to 30,000. Tube-bundle reactors having more than 40,000 catalyst tubes tend to be the exception. Within the container, the catalyst tubes are usually homogeneously distributed, the distribution expediently being chosen so that the distance between the central inner axes of adjacent catalyst tubes (i.e. the catalyst tube spacing) is from 35 to 45 mm (cf. EP-B 468290).

Particularly suitable heat exchange media are fluid thermostating media. The use of melts of salts, such as potassium nitrate, potassium nitrite, sodium nitrite and/or sodium nitrate, or of metals having a low melting point, such as sodium, mercury and alloys of various metals, is particularly advantageous.

As a rule, in all abovementioned configurations of the flow in the two-zone tube-bundle reactors, the flow velocity within the two required circulations of heat exchange media is chosen so that the temperature of the heat exchange medium increases from the point of entry into the reaction zone to the point of exit from the reaction zone by from 0 to 15° C., i.e. the abovementioned $\Delta T$ may be, according to the invention, from 1 to 10° C. or from 2 to 8° C. or from 2 to 6° C.

In a novel two-zone procedure, the temperature of the heat exchange medium on entering the reaction zone C is usually from 230 to 270° C. in the second reaction stage. The temperature of the heat exchange medium on entering the reaction zone D is, according to the invention, usually on the one hand from 250° C. to 300° C. and, on the other hand, simultaneously at least 10° C. above the temperature of the heat exchange medium entering the reaction zone C.

Preferably, the temperature of the heat exchange medium on entering the reaction zone D is at least 20° above the temperature of the heat exchange medium entering the reaction zone C. The difference between the temperatures on entry into the reaction zones C and D may thus be, according to the invention, up to 15° C., up to 25° C., up to 30° C., up to 35° C. or up to 40° C. Usually, however, the abovementioned temperature is not more than 50° C. The higher the chosen acrolein loading of the catalyst bed 2 in the novel process, the greater should be the difference between the temperature of the heat exchange-medium on entering the reaction zone C and the temperature of the heat exchange medium on entering the reaction zone D. Preferably, the temperature on entering the reaction zone C is from 245 to 260° C. and the temperature on entering the reaction zone D is from 265 to 285° C.

In the novel process, the two reaction zones C, D can of course also be realized in tube-bundle reactors spatially separated from one another. If required, a heat exchanger may also be mounted between the two reaction zones C, D. The two reaction zones C, D can of course also be designed as a fluidized bed.

Furthermore, in the novel process, it is also possible very generally to use catalyst beds 2 whose volume-specific activity in the direction of flow of the reaction gas mixture increases continuously, abruptly or stepwise (this may be reflected, for example, by dilution with inert material or variation of the activity of the multimetal oxide).

The inert diluent gases (e.g. only propane or only methane, etc.) recommended in EP-A 293224 and in EP-B 257565 may also be used for the novel procedure of the second reaction stage. Said diluent gases can, if required, also be combined with a volume-specific activity of the catalyst bed 2 decreasing in the direction of flow of the reaction gas mixture.

It should once again be pointed out here that in particular the two-zone tube-bundle reactor type described in German published application DE-B 2,201,528 may be used for carrying out the second reaction stage of the novel process, which reactor type provides the possibility of transferring a part of the relatively hot heat exchange medium of reaction zone D to the reaction zone C in order, if required, to heat up a reaction gas starting mixture 2 which is too cold or a cold recycled gas. Furthermore, the tube-bundle characteristic within an individual reaction zone can be designed as described in EP-A 382 098.

The novel process can of course also be realized in a single two-zone tube-bundle reactor as described, for example, in DE-C 2830765, EP-A 911313 and EP-A 383224, so the first reaction stage is implemented in the first reaction zone and the second reaction stage in the second reaction zone of the two-zone tube-bundle reactor.

The novel process is particularly suitable for a continuous procedure. It is surprising that it permits good selectivities in the formation of the desired produce in a single pass with high loading of the fixed bed catalysts with starting materials.

The novel process gives not the acrylic acid in pure form but a mixture from whose secondary components the acrylic acid can be separated in a manner known per se (for example by rectification and/or crystallization). Unconverted acrolein, and propene and inert diluent gas used and/or formed in the course of the reaction can be recycled to the gas-phase oxidation. In the novel two-stage gas-phase oxidation starting from propene, the recycling is expediently effected into the first oxidation stage. If required, the novel procedure can of course also be used in the case of conventional propene loadings.

Otherwise, in this publication conversion, selectivity and residence time are defined as follows, unless stated otherwise:

$$\text{Conversion of starting material (\%)} = \frac{\text{Number of moles of starting material converted}}{\text{Number of moles of starting material used}} \times 100$$

$$\text{Selectivity of product formation} = \frac{\text{Number of moles of starting material converted to product}}{\text{Number of moles of starting material converted}} \times 100$$

-continued $$\text{Residence time (sec.)} = \frac{\text{Empty reactor volume filled with catalyst (1)}}{\text{Throughput of reaction gas starting mixture (1 }(S.T.P)/h\text{)}} \times 3600$$

EXAMPLES AND COMPARATIVE EXAMPLES a) Preparation of a Novel Fixed-bed Catalyst 1

1. Preparation of Starting Material 1

209.3 kg of tungstic acid (72.94% by weight of W) were stirred, a little at a time, at 25° C., into 775 kg of an aqueous bismuth nitrate solution containing nitric acid (11.2% by weight of Bi, from 3 to 5% by weight of free nitric acid; density: from 1.22 to 1.27 g/mol). The resulting aqueous mixture was then stirred for a further 2 hours at 25° C. and then spray-dried.

The spray-drying was carried out in a rotating-disk spray tower by the cocurrent method at a gas outlet temperature of 300±10° C. and a gas outlet temperature of 100±10° C. The spray-dried powder obtained was then calcined at from 780 to 810° C. (in a rotary tubular furnace through which air flowed (1.54 m³ internal volume, 200 m³ (S.T.P.) of air/h)). What is important with regard to the exact setting of the calcination temperature is that it is tailored to the desired phase composition of the calcination product. The phases $WO_3$ (monoclinic) and $Bi_2W_2O_9$ are desired; the presence of $\gamma$-$Bi_2WO_6$ (russellite) is undesired. Consequently, if the compound $\gamma$-$Bi_2WO_6$ is still detectable after the calcination on the basis of a reflection in the powder x-ray diffraction pattern at a reflection angle of $2\theta=28.4°$ (CuK$\alpha$ radiation), the preparation should be repeated and the calcination temperature should be increased within the stated temperature range until the reflection disappears. The preformed calcined mixed oxide thus obtained was milled so that the $X_{50}$ value (cf. Ullmann's Encyclopedia of Industrial Chemistry, 6$^{th}$ Edition (1998) Electronic Release, Section 3.1.4 or DIN 66141) of the resulting particles was 5 $\mu$m. The milled material was then mixed with 1% by weight (based on the milled material) of finely divided $SiO_2$ (bulk density 150 g/l; $X_{50}$ value of the $SiO_2$ particles was 10 $\mu$m and the BET surface area was 100 m²/g).

2. Preparation of a Starting Material 2

A solution A was prepared by dissolving 213 kg of ammonium heptamolybdate in 600 l of water at 60° C. while stirring, and adding 0.97 kg of an aqueous potassium hydroxide solution (46.8% by weight of KOH) at 20° C. to the resulting solution while maintaining 60° C. and stirring.

A solution B was prepared by introducing 116.25 kg of an aqueous iron nitrate solution (14.2% by weight of Fe) into 262.9 kg of an aqueous cobalt nitrate solution (12.4% by weight of Co) at 60° C. The solution B was then pumped continuously into the initially taken solution A over a period of 30 minutes while maintaining the 60° C. Stirring was then carried out for 15 minutes at 60° C. Thereafter, 19.16 kg of a silica gel (46.80% by weight of $SiO_2$, density: from 1.36 to 1.42 g/ml, pH from 8.5 to 9.5, alkali metal content max. 0.5% by weight) were added to the resulting aqueous mixture and stirring was then carried out for a further 15 minutes at 60° C.

Spray drying was then carried out in a rotating-disk spray tower by the cocurrent method (gas inlet temperature: 400±10° C., gas outlet temperature: 140±5° C.). The resulting spray-dried powder had a loss on ignition of about 30% by weight (3 h at 600° C.).

3. Preparation of the Multimetal Oxide Active Material

The starting material 1 was homogeneously mixed with the starting material 2 in the amount required for the multimetal oxide active material having the stoichiometry $$[Bi_2W_2O_9.2WO_3]0.5[Mo_{12}Co_{5.5}Fe_{2.94}Si_{1.59}K_{0.08}O_x]_1$$

Based on the abovementioned total material, in addition 1.5% by weight of finely divided graphite (sieve analysis: min. 50% by weight <24 $\mu$m, max. 10% by weight >24 $\mu$m and <48 $\mu$m, max. 5% by weight >48 $\mu$m, BET surface area: from 6 to 13 m²/g) were mixed in homogeneously. The resulting dry blend was compressed to give hollow cylinders having a length of 3 mm, an external diameter of 5 mm and a wall thickness of 1.5 mm and then subjected to heat treatment as follows.

In a muffle furnace through which air flowed (60 l internal volume, 1 l/h of air per gram of active material precursor), heating was carried out at a heating rate of 180° C./h, initially from room temperature (25° C.) to 190° C. This temperature was maintained for 1 h and then increased to 210° C. at a heating rate of 60° C./h. The 210° C. were in turn maintained for 1 h before being increased at a heating rate of 60° C./h to 230° C. This temperature was likewise maintained for 1 h before it was increased to 265° C., once again at a heating rate of 60° C./h. The 265° C. were then likewise maintained for 1 h. Thereafter, cooling was first carried out to room temperature, and the decomposition phase was thus essentially complete. Thereafter, heating was carried out at a heating rate of 180° C./h to 465° C. and this calcination temperature was maintained for 4 h. A bed of the resulting unsupported catalyst rings formed a novel fixed-bed catalyst 1.

b) Preparation of a Novel Fixed-bed Catalyst 2

1. Preparation of the Catalytically Active Oxide Material $Mo_{12}V_3W_{1.2}Cu_{2.4}O_n$ 190 g of copper(II) acetate monohydrate were dissolved in 2700 g of water to give a solution I. 860 g of ammonium heptamolybdate tetrahydrate, 143 g of ammonium metavanadate and 126 g of ammonium paratungstate heptahydrate were dissolved in succession in 5500 g of water at 95° C. to give a solution II. Thereafter, the solution I was stirred all at once into the solution II, and then ≧25% strength by weight aqueous $NH_3$ solution was added in an amount sufficient to form a solution again. This was spray-dried at an outlet temperature of 110° C. The resulting spray-dried powder was kneaded with 0.25 kg of a 30% strength by weight aqueous acetic acid solution per kg of powder using a kneader of type ZSl-80 from Werner & Pfleiderer, and then dried at 110° C. for 10 h in a drying oven.

700 g of the catalyst precursor thus obtained were calcined in an air/nitrogen mixture [(200 l of $N_2$/15 l of air)/h] in a rotary tubular furnace (50 cm long, 12 cm internal diameter). During the calcination, the kneaded material was first heated continuously from room temperature (about 25° C.) to 325° C. in the course of one hour. This temperature was then maintained for 4 h. Heating was then carried out to 400° C. in the course of 15 minutes, this temperature was maintained for 1 h and cooling was then effected to room temperature.

The calcined catalytically active material was milled to give a finely divided powder, 50% of whose particles passed through a sieve of mesh size from 1 to 10 $\mu$m and whose fraction of particles having a maximum dimension greater than 50 $\mu$m was less than 1%.

2. Preparation of Coated Catalyst 28 kg of annular supports (7 mm external diameter, 3 mm length, 4 mm internal diameter, steatite, having a surface roughness Rz according to EP-B 714700 of 45 μm and having a total pore volume, based on the volume of the supports, of ≦1% by volume, manufacturer: Caramtec DE) were introduced into a coating pan (angle of inclination 90°; Hicoater from Lödige, DE) having an internal volume of 200 l. The coating pan was then rotated at 16 rpm. 2000 g of an aqueous solution consisting of 75% by weight of $H_2O$ and 25% by weight of glycerol were sprayed onto the supports via a nozzle in the course of 25 minutes. At the same time, 7 kg of the catalytically active oxide powder from a) were continuously metered in via a vibrating channel outside the spray cone of the atomizer nozzle in the same period. During the coating, the powder fed in was completely adsorbed onto the surface of the supports, and no agglomeration of the finely divided oxide active material was observed. After the end of the addition of powder and aqueous solution, hot air at 110° C. was blown into the coating pan for 20 minutes at a speed of 2 rpm. Drying was then carried out for a further 2 hours at 250° C. in the stationary bed (tray drier) under air. Annular coated catalysts whose proportion of oxide active material was 20% by weight, based on the total material, were obtained. The coat thickness was 230±25 μm, both over the surface of one support and over the surface of different supports. A bed of the resulting coated catalyst rings formed a novel fixed-bed catalyst 2.

Preparation of a Spherical Comparative Fixed-bed Coated Catalyst 1

1. Preparation of a Staring Material 1

209.3 kg of tungstic acid (72.94% by weight of W) were stirred, a little at a time, at 25° C., into 775 kg of an aqueous bismuth nitrate solution containing nitric acid (11.2% of Bi, from 3 to 5% by weight of free nitric acid; density: from 1.22 to 1.27 g/ml). The resulting aqueous mixture was then stirred for a further 2 hours at 25° C. and then spray-dried.

The spray-drying was carried out in a rotating-disk spray tower by the cocurrent method at a gas inlet temperature of 300±10° C. and a gas outlet temperature of 100±10° C. The spray-dried powder obtained was then calcined at from 780 to 810° C. (in a rotary tubular furnace through which air flowed (1.54 m³ internal volume, 200 m³ (S.T.P.) of air/h)). What is important with regard to the exact setting of the calcination temperature is that it should be tailored to the desired phase composition of the calcination product. The phases $WO_3$ (monoclinic) and $Bi_2W_2O_9$ are desired; the presence of γ-$Bi_2WO_6$ (russelite) is undesired. Consequently, if this compound γ-$Bi_2WO_6$ is still detectable after the calcination on the basis of a reflection in the powder X-ray diffraction pattern at a reflection angle of 2θ=28.4° C. (CuKα radiation), the preparation should be repeated and the calcination temperature should be increased within the stated temperature range until the reflection disappears. The preformed calcined mixed oxide thus obtained was milled so that the $X_{50}$ value (cf. Ullmann's Encyclopedia of Industrial Chemistry, 6$^{th}$ Edition (1998) Electronic Release, Section 3.1.4 or DIN 66141) of the resulting particles was 5 μm. The milled material was then mixed with 1% by weight (based on the milled material) of finely divided $SiO_2$ (bulk density 150 g/l; $X_{50}$ value of the $SiO_2$ particles was 10 μm, the BET surface area was 100 m²/g.

2. Preparation of a Starting Material 2

A solution A was prepared by dissolving 213 kg of ammonium heptamolybdate in 600 l of water at 60° C. while stirring, and adding 0.97 kg of an aqueous potassium hydroxide solution (46.8% by weight of KOH) at 20° C. to the resulting solution while maintaining 60° C. and stirring.

A solution B was prepared by introducing 116.25 kg of an aqueous iron nitrate solution (14.2% by weight of Fe) into 262.9 kg of an aqueous cobalt nitrate solution (12.4% by weight of Co) at 60° C. The solution B was then pumped continuously into the initially taken solution A over a period of 30 minutes while maintaining the 60° C. Stirring was then carried out for 15 minutes at 60° C. Thereafter, 19.16 kg of a silica gel (46.80% by weight of $SiO_2$, density: from 1.36 to 1.42 g/ml, pH from 8.5 to 9.5, akali metal content max. 0.5% by weight) were added to the resulting aqueous mixture and stirring was then carried out for a further 15 minutes at 60° C.

Spray drying was then carried out in a rotating-disk spray tower by the countercurrent method (gas inlet temperature: 400±10° C., gas outlet temperature: 140±5° C.). The resulting spray-dried powder had a loss on ignition of about 30% by weight (ignition for 3 h at 600° C.).

3. Preparation of the Multimetal Oxide Active Material

The starting material 1 was homogeneously mixed with the starting material 2 in the amount required for a multimetal oxide active material having the stoichiometry

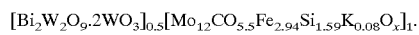

Based on the abovementioned total material, in addition 1.5% by weight of finely divided graphite (sieve analysis: min. 50% by weight <24 μm, max. 10% by weight >24 μm and <48 μm, max. 5% by weight >48 μm, BET surface area: from 6 to 13 m²/g) were homogeneously mixed in. The resulting dry blend was compressed to give hollow cylinders having a length of 3 mm, an external diameter of 5 mm and a wall thickness of 1.5 mm and then subjected to a heat treatment as follows.

In a muffle furnace through which air flowed (60 l internal volume, 1 l/h of air per gram of active material precursor), heating was carried out at a heating rate of 180° C./h, initially from room temperature (25° C.) to 190° C. This temperature was maintained for 1 h and then increased to 210° C. at a heating rate of 60° C./h. The 210° C. were in turn maintained for 1 h before being increased at a heating rate of 60° C./h to 230° C. This temperature was likewise maintained for 1 h before it was increased to 265° C., once again at a heating rate of 60° C./h. The 265° C. were then likewise maintained for 1 h. Thereafter, cooling was initially effected to room temperature and the decomposition phase was thus essentially complete. Thereafter, heating was carried out at a heating rate of 180° C./h to 465° C. and this calcination temperature was maintained for 4 h.

The calcined catalytically active material was milled to a finely divided powder, 50% of whose particles passed through a sieve of mesh size from 1 to 10 μm and whose proportion of particles having a maximum dimension above 50 μm was less than 1%.

4. Preparation of Coated Catalyst 30 kg of spherical supports (4–5 mm diameter, having a surface roughness Rz according to EP-B 714700 of 45 μm and having a total pore volume, based on the volume of the supports, of ≦1% by volume, manufacturer: Ceramtec DE) were introduced into a coating pan (angle of inclination 90°; Hicoater from Lödige, DE) of 200 l internal volume. The coating pan was then rotated at 16 rpm. 2500 g of an aqueous solution consisting of 75% of $H_2O$ and 25% by weight of glycerol were sprayed onto the supports via a nozzle in the course of 25 minutes. At the same time, 13 kg of the catalytically active oxide powder from a) were metered in continuously via a vibrating channel outside the spray cone of the atomizer nozzle in the same period. During the coating, the powder fed in was adsorbed completely onto the surface of the supports and no agglomeration of the finely divided oxide active material was observed. After the end of the addition of powder and aqueous solution, hot air at 110° C. was blown into the coating pan for 20 minutes at a speed of 2 rpm. Drying was then carried out for a further 2 hours at 250° C. in the stationary bed (tray drier) under air. Spherical coated catalysts whose proportion of oxide active material was 30%, based on the total material, were obtained. The coat thickness was 280±25 μm, both over the surface of one support and over the surface of different supports. A bed of the resulting coated catalyst beads formed the spherical comparative fixed-bed coated catalyst 1.

d) Preparation of a Spherical Comparative Fixed-bed Coated Catalyst 2

1. Preparation of the Catalytically Active Oxide Material $Mo_{12}V_3W_{1.2}Cu_{2.4}O_n$ 190 g of copper(II) acetate monohydrate were dissolved in 2700 g of water to give a solution I. 860 g of ammonium heptamolybdate tetrahydrate, 143 g of ammonium metavanadate and 126 g of ammonium paratungstate heptahydrate were dissolved in succession in 5500 g of water at 95° C. to give a solution II. Thereafter, the solution I was stirred all at once into the solution II and then a 25% strength by weight aqueous $NH_3$ solution was added in an amount sufficient to form a solution again. This was spray-dried at an outlet temperature of 110° C. The resulting spray-dried powder was kneaded with 0.25 kg of a 30% strength by weight aqueous acetic acid solution per kg of powder using a kneader of type ZSl-80 from Werner & Pfleiderer and then dried at 110° C. for hours in a drying oven. 700 g of the catalyst precursor thus obtained were calcined in an air/nitrogen mixture [(200 l of $N_2$/15 l of air)/h] in a rotary tubular furnace (50 cm long, 12 cm internal diameter). During the calcination, the kneaded material was first heated continuously from room temperature (about 25° C.) to 325° C. in the course of 1 hour. This temperature was then maintained for 4 hours. Thereafter, heating was carried out to 400° C. in the course of 15 minutes, this temperature was maintained for 1 hour and cooling to room temperature was then effected.

The calcined catalytically active material was milled to give a finely divided powder, 50% of whose particles passed through a sieve of mesh size from 1 to 10 μm and whose proportion of particles having a maximum dimension above 50 μm was less than 1%.

2. Preparation of Coated Catalyst 30 kg of spherical supports (4–5 mm diameter, steatite, having a surface roughness Rz according to EP-B 714700 of 45 μm and having a total pore volume, based on the volume of the supports, of ≦1% by volume, manufacturer: Caramtec DE) were introduced into a coating pan (angle of inclination 90°; Hicoater from Lödige, DE) of 200 l internal volume. The coating pan was then rotated at 16 rpm. 1600 g of an aqueous solution were then sprayed onto the supports via a nozzle in the course of 25 minutes. At the same time, 5.3 kg of the catalytically active oxide powder from a) were metered in continuously via a vibrating channel outside the spray cone of the atomizer nozzle in the same period. During the coating, the powder fed in was completely adsorbed onto the surface of the supports and no agglomeration of the finely divided oxide active material was observed. After the end of the addition of powder and aqueous solution, hot air at 110° C. was blown into the coating pan for 20 minutes at a speed of 2 rpm. Spherical coated catalysts whose proportion of oxide active material was 15% by weight, based on the total material, were obtained. The coat thickness was 210±5 μm, both over the surface of one support and over the surface of different supports. A bed of the resulting coated catalyst beads formed the spherical comparative fixed-bed coated catalyst 2.

e) Preparation of a Comparative Fixed-bed Cylindrical Unsupported Catalyst 1

1. Preparation of a Starting material 1

209.3 kg of tungstic acid (72.94% by weight of W) were stirred at 25° C. into 775 kg of an aqueous bismuth nitrate solution containing nitric acid (11.2% by weight of Bi, from 3 to 5% by weight of free nitric acid; density: from 1.2 to 1.27 g/l). The resulting aqueous mixture was then stirred for a further 2 hours at 25° C. and then spray-dried.

The spray drying was carried out in a rotating-disk spray tower by the cocurrent method at a gas inlet temperature of 300±10° C. and a gas outlet temperature of 100±10° C. The spray-dried powder obtained was then calcined at from 780 to 810° C. (in a rotary tubular furnace through which air flowed (1.54 m³ internal volume, 200 m³ (S.T.P.) of air/h)). What is important with regard to the exact setting of the calcination temperature is that it should be tailored to the desired phase composition of the calcination product. The phases $WO_3$ (monoclinic) and $Bi_2W_2O_9$ are desired; the presence of $\gamma$-$Bi_2WO_6$ (russellite) is undesired. Consequently, if the compound $\gamma$-$Bi_2WO_6$ is still detectable after the calcination on the basis of a reflection in the powder X-ray diffraction pattern at a reflection angle of 2θ=28.4° (CuKα radiation), the preparation should be repeated and the calcination temperature should be increased within the stated temperature range until the reflection disappears. The preformed calcined mixed oxide thus obtained was milled so that the $X_{50}$ value (cf. Ullmann's Encyclopedia of Industrial Chemistry, 6$^{th}$ Edition (1998) Electronic Release, Section 3.1.4 or DIN 66141) of the resulting particles was 5 μm. The milled material was then mixed with 1% by weight (based on the milled material) of finely divided $SiO_2$ (bulk density 150 g/l; $X_{50}$ value of the $SiO_2$ particles was 10 μm, the BET surface area was 100 m²/g).

2. Preparation of a Starting Material 2

A solution A was prepared by dissolving 213 kg of ammonium heptamolybdate in 600 l of water at 60° C. while stirring, and adding 0.97 kg of an aqueous potassium hydroxide solution (46.8% by weight of KOH) at 20° C. to the resulting solution while maintaining the 60° C. and stirring.

A solution B was prepared by introducing 116.25 kg of an aqueous iron nitrate solution (14.2% by weight of Fe) into 262.9 kg of an aqueous cobalt nitrate solution (12.4% by weight of Co) at 60° C.

While maintaining the 60° C., the solution B was pumped continuously into the initially taken solution A over a period of 30 minutes. Stirring was then carried out for 15 minutes at 60° C. 19.16 kg of a silica gel (46.80% by weight of $SiO_2$, density: 1.36 to 1.42 g/ml, pH from 8.5 to 9.5, alkali metal content max. 0.5% by weight) were then added to the resulting aqueous mixture and stirring was then carried out for a further 15 minutes at 60° C.

Spray drying was then carried out in a rotating-disk spray tower by the cocurrent method (gas inlet temperature: 400±10° C., gas outlet temperature: 140±5° C.). The resulting spray-dried powder had a loss on ignition of about 30% by weight (3 h at 600° C.).

3. Preparation of the Multimetal Oxide Active Material

The starting material 1 was homogeneously mixed with the starting material 2 in the amount required for a multimetal oxide active material having the stoichiometry

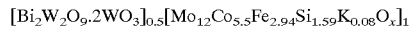

$[Bi_2W_2O_9.2WO_3]_{0.5}[Mo_{12}Co_{5.5}Fe_{2.94}Si_{1.59}K_{0.08}O_x]_1$

Based on the abovementioned total material, in addition 1.5% by weight of finely divided graphite (sieve analysis: min. 50% by weight <24 μm), max. 10% by weight >24 μm and <48 µm, max. 5% by weight >48 µm, BET surface area: from 6 to 13 m²/g) were homogeneously mixed in. The resulting dry blend was compressed to give solid cylinders having a length of 3 mm and an external diameter of 5 mm and then subjected to a heat treatment as follows.

In a muffle furnace through which air flowed (60 l internal volume, 1 l/h of air per gram of active material precursor), heating was carried out at a heating rate of 150° C./h, initially from room temperature (25° C.) to 180° C. This temperature was maintained for 1.5 hours and then increased at a heating rate of 60° C./h to 200° C. The 200° C. were in turn maintained for 1.5 hours before they were increased at a heating rate of 60° C./h to 220° C. This temperature was likewise maintained for 1.5 hours before it was increased to 250° C., once again at a heating rate of 60° C./h. The 250° C. were then likewise maintained for 1.5 hours. Thereafter, cooling was first effected to room temperature and the decomposition phase was thus essentially complete. Thereafter, heating was carried out at a heating rate of 180° C./h to 465° C. and this calcination temperature was maintained for 4 hours. A bed of the resulting unsupported catalyst formed the comparative fixed-bed catalyst 1 in the form of solid cylinders.

f) Preparation of a Comparative Fixed-bed Catalyst 2 in the Form of Solid Cylinders 1. Preparation of the Catalytically Active Oxide Material $Mo_{12}V_3W_{1.2}Cu_{2.4}O_n$ 190 g of copper(II) acetate monohydrate were dissolved in 2700 g of water to give a solution I. 860 g of ammonium heptamolybdate tetrahydrate, 143 g of ammonium metavanadate and 126 g of ammonium paratungstate heptahydrate were dissolved in succession in 5500 g of water at 95° C. to give a solution II. Thereafter, the solution I was stirred all at once into the solution II and then a 25% strength by weight aqueous $NH_3$ solution was added in an amount sufficient to form a solution again. This was spray-dried at an outlet temperature of 110° C. The resulting spray-dried powder was kneaded with 0.25 kg of a 30% strength by weight aqueous acetic acid solution per kg of powder using a kneader of type ZSl-80 from Werner & Pfleiderer and then dried at 110° C. for 10 hours in a drying oven.

700 g of the catalyst precursor thus obtained were calcined in an air/nitrogen mixture [(200 l of $N_2$/15 l of air)/h] in a rotary tubular furnace (50 cm long, 12 cm internal diameter). During the calcination, the kneaded material was first heated continuously from room temperature (about 25° C.) to 325° C. in the course of 1 hour. This temperature was then maintained for 4 hours. Thereafter, heating was carried out to 400° C. in the course of 15 minutes, this temperature was maintained for 1 hour and cooling was then effected to room temperature.

The calcined catalytically active material was milled to give a finely divided powder, 50% of whose particles passed through a sieve of mesh size from 1 to 10 µm and whose proportion of particles having a maximum dimension above 50 µm was less than 1%.

After admixing 3% by weight (based on the active material) of graphite, the catalytically active material thus obtained was compressed to give solid cylinders having a length of 3 mm and an external diameter of 5 mm.

A bed of the resulting unsupported catalysts formed the comparative fixed-bed catalyst 2 in the form of solid cylinders.

g) Gas-phase Catalytic Oxidation of Propene to Acrylic Acid

1. The First Reaction Stage

A first reaction tube (V2A stainless steel; 30 mm external diameter; 2 mm wall thickness; 26 mm internal diameter, length: 439 cm, having a thermal tube (4 mm external diameter) centered in the middle of the reaction tube for receiving a thermocouple with which the temperature in the reaction tube can be determined) was loaded from bottom to top on a catalyst support ledge (44 cm long), first with steatite beads having a rough surface (from 4 to 5 mm diameter; inert material for heating the reaction gas starting mixture 1) over a length of 30 cm and then with fixed-bed catalyst 1 prepared in a) (or in c) or in e)) over a length of 300 cm, before the loading was completed over a length of 30 cm with the abovementioned steatite beads as a subsequent bed. The remaining 35 cm of catalyst tube were left empty.

That part of the first reaction tube which had been loaded with solid was thermostated by means of 12 aluminum blocks cast in cylindrical form around the tube and each having a length of 30 cm and being heated by electrical heating tapes (comparative experiments with a corresponding reaction tube heated by means of a salt bath through which nitrogen was bubbled showed that the thermostating by means of aluminum block was capable of simulating thermostating by means of a salt bath). The first six aluminum blocks in the direction of flow defined a reaction zone A and the remaining aluminum blocks defined a reaction zone B. Those ends of the reaction tube which were free of solid were kept at 220° C. by means of steam under superatmospheric pressure.

2. The Second Reaction Stage

A second reaction tube (V2A stainless steel; 30 mm external diameter; 26 mm wall thickness; 26 mm internal diameter, length: 439 cm, having a thermal tube (4 mm external diameter) centered in the middle of the reaction tube for receiving a thermocouple with which the temperature in the reaction tube can be determined) was loaded from bottom to top on a catalyst support ledge (44 cm long), first with steatite beads having a rough surface (from 4 to 5 mm diameter; inert material for heating the reaction gas starting mixture 2) over a length of 30 cm and then with the fixed-bed catalyst prepared in b) (or in d) or f)) over a length of 300 cm, before the loading was complete over a length of 30 cm with the abovementioned steatite beads as a preliminary bed. The remaining 35 cm of catalyst tube were left empty.

That part of the second reaction tube which had been loaded with solid was thermostated by means of 12 aluminum blocks cast in cylindrical form around the tube and each having a length of 30 cm (comparative experiments with a corresponding reaction tube heated by means of a salt bath through which nitrogen was bubbled showed that the thermostating by means of aluminum block was capable of simulating thermostating by means of a salt bath). The first six aluminum blocks in the direction of flow defined a reaction zone C and the remaining six aluminum blocks defined a reaction zone D. Those ends of the reaction tube which were free of solid were kept at 220° C by means of steam under superatmospheric pressure.

3. The Gas-phase Oxidation

The first reaction tube described above was fed continuously with a reaction gas starting mixture having the following composition, the loading and the thermostating of the first reaction tube being varied:

from 6 to 6.5% by volume of propene,
from 3 to 3.5% by volume of $H_2O$,
from 0.3 to 0.5% by volume of CO,
from 0.8 to 1.2% by volume of $CO_2$,
from 0.025 to 0.04% by volume of acrolein and
from 10.4 to 10.7% by volume of $O_2$,
the remaining amount to 100% comprising molecular nitrogen.

A small sample of the product gas mixture of the first reaction stage was taken at the outlet of the first reaction tube for a gas chromatographic analysis. Otherwise, the product gas mixture was fed directly to the subsequent acrolein oxidation stage (oxidation to acrylic acid) with introduction of air at 25° C. through a nozzle (reaction stage 2). A small sample of the product gas mixture of the acrolein oxidation stage was likewise taken for gas chromatographic analysis. Otherwise, the acrylic acid was separated from the product gas mixture of the second reaction stage in a manner known per se, and a part of the residual gas was re-used for loading the propene oxidation stage (i.e. as recycle gas), which explains the acrolein content of the abovementioned feed gas and the small variants in the feed composition.

The pressure at the entrance of the first reaction tube varied, as a function of the chosen propene loading, in a range from 3.0 to 0.9 bar. An analysis point was also present at the end of the reaction zones A, C. The pressure at the entrance of the second reaction tube varied, as a function of the acrolein loading, in the range from 2 to 0.5 bar.

The results achieved for the various catalyst beds as a function of the chosen loadings and of the chosen aluminum thermostating and the air feed implemented (after the first reaction stage) are shown on the tables below (the top example can, according to the invention, also be carried out in one-zone tubular reactors in a corresponding manner (i.e. for example with the same loading); the temperature in the first stage should then expediently be from 320 to 360° C. and that in the second stage from 245 to 275° C.; in this context, it is furthermore advisable, in the first reaction stage, to replace the 300 cm bed of fixed-bed catalyst 1 by the following bed extending only over a length of 270 cm: in the direction of flow, first a mixture of 65% by volume of fixed-bed catalyst 1 and 35% by volume of steatite rings (external diameter×internal diameter×length =5 mm×3 mm×2 mm) over a length of 100 cm and then a mixture of 90% by volume of fixed-bed catalyst 1 and 10% by volume of the above steatite rings over a length of 170 cm; it was also advisable in this context, in the second reaction stage, to replace the 300 cm bed of the fixed-bed catalyst 2 by the following bed of corresponding length: in the direction of flow, first a mixture of 70% by volume of fixed-bed catalyst 2 and 30% by volume of steatite rings (external diameter× internal diameter×length =7 mm×3 mm×4 mm) over a length of 100 cm and then 200 cm of pure fixed-bed catalyst 2).

$T_A$, $T_B$, $T_C$ and $T_D$ are the temperatures of the aluminum blocks in the reaction zones A, B, C and D.

$C_{PA}$ is the propene conversion at the end of the reaction zone A.

$C_{PB}$ is the propene conversion at the end of the reaction zone B.

$S_{DP}$ is the selectivity of the acrolein formation and of the acrylic acid byproduct formation together after the first reaction stage and based on propene converted.

$C_{AC}$ is acrolein conversion at the end of the reaction zone C.

$C_{AD}$ is the acrolein conversion at the end of the reaction zone D.

$C_{PD}$ is the propene conversion at the end of the reaction zone D.

$S_{AA}$ is the selectivity of the acrylic acid formation after the second reaction stage and based on propene converted.

$STY_{AA}$ is the space-time yield of acrylic acid at the exit of the second reaction tube.

R is the molar ratio of molecular oxygen to acrolein in the reaction gas starting mixture 2

M is the amount of air fed in through a nozzle after the first reaction stage.

TABLE 1

Catalyst bed: novel fixed-bed catalyst 1/novel fixed-bed catalyst 2

| Propene loading [1 (S.T.P.) of propene/ 1 · h] | $T_A$ [° C.] | $T_B$ [° C.] | $C_{PA}$ (%) | $C_{PB}$ (%) | $S_{DP}$ (%) | M (1 (S.T.P.)/ h) | R |
|---|---|---|---|---|---|---|---|
| 160 | 319 | 329 | 69.3 | 94.5 | 94.4 | 420 | 1.39 |
| 175 | 325 | 336 | 74.8 | 94.55 | 95.5 | 520 | 1.49 |
| 200 | 333 | 344 | 72.7 | 94.4 | 95.5 | 640 | 1.54 |

| Acrolein loading [1 (S.T.P.) of acrolein/ 1 · h] | $T_C$ [° C.] | $T_D$ [° C.] | $C_{AC}$ (%) | $C_{AD}$ (%) | $C_{PD}$ (%) | $S_{AA}$ (%) | $STY_{AA}$ (g/1 · h) |
|---|---|---|---|---|---|---|---|
| 139 | 255 | 276 | 50.9 | 99.2 | 94.4 | 95.2 | 228 |
| 152 | 261 | 277 | 77.3 | 99.2 | 94.5 | 95.8 | 255 |
| 173 | 261 | 281 | 72.6 | 99.3 | 94.4 | 95.7 | 291 |

TABLE 2

Catalyst bed: comparative fixed-bed coated catalyst 1/comparative fixed-bed coated catalyst 2

| Propene loading [1 (S.T.P.) of propene/ 1 · h] | $T_A$ [° C.] | $T_B$ [° C.] | $C_{PA}$ (%) | $C_{PB}$ (%) | $S_{DP}$ (%) | M (1 (S.T.P.)/ h) | R |
|---|---|---|---|---|---|---|---|
| 160 | 342 | 366 | 65.2 | 93.4 | 93.1 | 410 | 1.47 |
| 175 | 350 | 380 | 73.1 | 93.0 | 92.9 | 515 | 1.52 |
| 200 | 360 | 385 | 69.7 | 92.8 | 92.5 | 645 | 1.59 |

| Acrolein loading [1 (S.T.P.) of acrolein/ 1 · h] | $T_C$ [° C.] | $T_D$ [° C.] | $C_{AC}$ (%) | $C_{AD}$ (%) | $C_{PD}$ (%) | $S_{AA}$ (%) | $STY_{AA}$ (g/1 · h) |
|---|---|---|---|---|---|---|---|
| 130 | 255 | 268 | 59.1 | 99.1 | 93.4 | 94.3 | 206 |
| 141 | 263 | 279 | 67.2 | 98.9 | 93.0 | 94.0 | 220 |
| 159.6 | 265 | 285 | 69.1 | 98.7 | 92.8 | 93.8 | 248 |

TABLE 3

Catalyst bed: comparative fixed-bed unsupported cylindrical catalyst 1/comparative fixed-bed unsupported cylindrical catalyst 2

| Propene loading [1 (S.T.P.) of propene/ 1 · h] | $T_A$ [° C.] | $T_B$ [° C.] | $C_{PA}$ (%) | $C_{PB}$ (%) | $S_{DP}$ (%) | M (1 (S.T.P.)/ h) | R |
|---|---|---|---|---|---|---|---|
| 160 | 304 | 310 | 63.4 | 94.3 | 89.2 | 470 | 1.47 |
| 175 | 308 | 315 | 69.3 | 94.3 | 90.1 | 550 | 1.56 |
| 200 | 310 | 320 | 68.2 | 94.4 | 89.8 | 700 | 1.64 |

TABLE 3-continued

Catalyst bed: comparative fixed-bed unsupported cylindrical catalyst 1/comparative fixed-bed unsupported cylindrical catalyst 2

| Acrolein loading [l (S.T.P.) of acrolein/ l · h] | $T_C$ [° C.] | $T_D$ [° C.] | $C_{AC}$ (%) | $C_{AD}$ (%) | $C_{PD}$ (%) | $S_{AA}$ (%) | $STY_{AA}$ (g/l · h) |
|---|---|---|---|---|---|---|---|
| 131 | 250 | 259 | 72.3 | 99.3 | 94.3 | 93.1 | 205 |
| 142 | 254 | 263 | 67.3 | 99.3 | 94.3 | 93.3 | 223 |
| 160 | 258 | 267 | 69.2 | 99.3 | 94.4 | 92.8 | 250 |

We claim:

1. A process for the catalytic gas-phase oxidation of propene to acrylic acid, in which a reaction gas starting mixture 1 which comprises propene, molecular oxygen and at least one inert gas and contains the molecular oxygen and the propene in a molar $O_2:C_3H_6$ ratio of $\geq 1$ is first passed, in a first reaction stage at elevated temperatures, over a first fixed-bed catalyst whose active material is at least one multimetal oxide containing (1) at least one of molybdenum and tungsten, and (2) at least one of bismuth, tellurium, antimony, tin and copper, in such a way that the propene conversion in a single pass is $\geq 90$ mol % and the associated selectivity of the acrolein formation and of the acrylic acid byproduct formation together is $\geq 90$ mol %, the temperature of the product gas mixture leaving the first reaction stage is, if required, reduced by direct, indirect, or direct and indirect, cooling and, if required, molecular oxygen, inert gas, or molecular oxygen and inert gas, are added to the product gas mixture, and the product gas mixture, as reaction gas starting mixture 2 which comprises acrolein, molecular oxygen and at least one inert gas and contains the molecular oxygen and the acrolein in a molar $O_2:C_3H_4O$ ratio of $\geq 0.5$, is then passed, in a second reaction stage at elevated temperatures, over a second fixed-bed catalyst whose active material is at least one multimetal oxide containing molybdenum and vanadium, in such a way that the acrolein conversion in a single pass is $\geq 90$ mol % and the selectivity of the acrylic acid formation balanced over both reaction stages is $\geq 80$ mol %, based on propene converted, wherein
   a) the loading of the first fixed-bed catalyst with the propene contained in the reaction gas starting mixture 1 is $\geq 160$ l (S.T.P.) of propene/l of catalyst bed·h,
   b) the loading of the second fixed-bed catalyst with the acrolein contained in the reaction gas starting mixture 2 is $\geq 140$ l (S.T.P.) of acrolein/l of catalyst bed·h and
   c) both the geometry of the catalyst moldings of the first fixed-bed catalyst and the geometry of the catalyst moldings of the second fixed-bed catalyst are annular, with the proviso that
      the external ring diameter is from 2 to 11 mm,
      the ring length is from 2 to 11 mm and
      the wall thickness of the ring is from 1 to 5 mm.

2. A process for the catalytic gas-phase oxidation of propene to acrolein, acrylic acid, or acrolein and acrylic acid, in which a reaction gas starting mixture 1 which comprises propene, molecular oxygen and at least one inert gas and contains the molecular oxygen and the propene in a molar $O_2:C_3H_6$ ratio of $\geq 1$ is passed, in a reaction stage at elevated temperatures, over a first fixed-bed catalyst whose active material is at least one multimetal oxide containing (1) at least one of molybdenum and tungsten, and (2) at least one of bismuth, tellurium, antimony, tin and copper, in such a way that the propene conversion in a single pass is $\geq 90$ mol % and the associated selectivity of the acrolein formation and of the acrylic acid byproduct formation together is $\geq 90$ mol %, wherein
   a) the loading of the fixed-bed catalyst with the propene contained in the reaction gas starting mixture 1 is $\geq 160$ l (S.T.P.) of propene/l of the catalyst bed·h and
   b) the geometry of the catalyst moldings of the fixed-bed catalyst is annular, with the proviso that
      the external diameter of the ring is from 2 to 11 mm,
      the ring length is from 2 to 11 mm and
      the wall thickness of the ring is from 1 to 5 mm.

3. The process according to claim 1, wherein the first fixed-bed catalyst is unsupported and the second fixed-bed catalyst is coated.

4. The process according to claim 1, wherein the first fixed-bed catalyst is coated and the second fixed-bed catalyst is unsupported.

5. The process according to claim 1, wherein the first fixed-bed catalyst is unsupported and the second fixed-bed catalyst is unsupported.

6. The process according to claim 1, wherein the first fixed-bed catalyst is coated and the second fixed-bed catalyst is coated.

7. The process according to claim 6, wherein the external ring diameter is from 2 to 10 mm, the ring length is from 2 to 10 mm and the wall thickness of the ring is from 1 to 4 mm.

8. The process according to claim 7, wherein the external ring diameter is from 4 to 8 mm, the ring length is from 3 to 6 mm and the wall thickness of the ring is from 1 to 2 mm.

9. The process according to claim 8, wherein the external ring diameter is 7 mm, the ring length is 3 mm, and the internal diameter is 4 mm.

10. The process according to claim 6, wherein the coated catalysts are coated with a catalytically active oxide material having a thickness of from about 10 to 1000 μm.

11. The process according to claim 10, wherein the thickness is from about 50 to 500 μm.

12. The process according to claim 11, wherein the thickness is from about 100 to 500 μm.

13. The process according to claim 12, wherein the thickness is from about 150 to 250 μm.

14. The process according to claim 1, wherein the first fixed-bed catalyst has the following formula (I)

$$Mo_{12}Bi_aFe_bX^1_cX^2_dX^3_eX^4_fO_n \qquad (I),$$

where
   $X^1$ is at least one of nickel and cobalt,
   $X^2$ is at least one of thallium, an alkali metal and an alkaline earth metal,
   $X^3$ is at least one of zinc, phosphorus, arsenic, boron, antimony, tin, cerium, lead and tungsten,
   $X^4$ is at least one of silicon, aluminum, titanium and zirconium,
   a is from 0.5 to 5,
   b is from 0.01 to 5,
   c is from 0 to 10,
   d is from 0 to 2,
   e is from 0 to 8,
   f is from 0 to 10 and
   n is a number which is determined by the valency and frequency of the elements other than oxygen in I.

15. The process according to claim 1, wherein the first fixed-bed catalyst has the following formula (II)

$$[Y^1_aY^2_bO_x]_p[Y^3_cY^4_dY^5_eY^6_fY^7_gY^2_hO_y]_q \qquad (II)$$

where
   $Y^1$ is at least one of bismuth, tellurium, antimony, tin and copper,
   $Y^2$ is at least one of molybdenum and tungsten, $Y^3$ is at least one of an alkali metal, thallium and samarium, $Y^4$ is at least one of an alkaline earth metal, nickel, cobalt, copper, manganese, zinc, tin, cadmium and mercury, $Y^5$ is at least one of iron, chromium, cerium and vanadium, $Y^6$ is at least one of phosphorus, arsenic, boron and antimony, $Y^7$ is at least one of a rare earth metal, titanium, zirconium, niobium, tantalum, rhenium, ruthenium, rhodium, silver, gold, aluminum, gallium, indium, silicon, germanium, lead, thorium and uranium, a' is from 0.01 to 8, b' is from 0.1 to 30, c' is from 0 to 4, d' is from 0 to 20, e' is from 0 to 20, f' is from 0 to 6, g' is from 0 to 15, h' is from 8 to 16, x' and y' are numbers which are determined by the valency and frequency of the elements other than oxygen in II and p and q are numbers whose ratio p/q is from 0.1 to 10.

16. The process according to claim 1, wherein the first fixed-bed catalyst has the following formula (III)

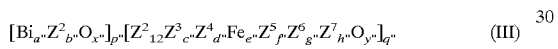 (III)

where $Z^2$ is at least one of molybdenum and tungsten, $Z^3$ is at least one of nickel and cobalt, $Z^4$ is at least one of thallium, an alkali metal and an alkaline earth metal, $Z^5$ is at least one of phosphorus, arsenic, boron, antimony, tin, cerium and lead, $Z^6$ is at least one of silicon, aluminum, titanium and zirconium, $Z^7$ is at least one of copper, silver and gold, a" is from 0.1 to 1, b" is from 0.2 to 2, c" is from 3 to 10, d" is from 0.02 to 2, e" is from 0.01 to 5, f" is from 0 to 5, g" is from 0 to 10, h" is from 0 to 1, x" and y" are numbers which are determined by the valency and frequency of the elements other than oxygen in III and p" and q" are numbers whose ratio p"/q" is from 0.1 to 5, preferably from 0.5 to 2.

17. The process according to claim 1, wherein the second fixed-bed catalyst has the following formula (IV)

$Mo_{12}V_aX^1_bX^2_cX^3_dX^4_eX^5_fX^6_gO_n$ (IV), where:

$X^1$ is at least one of W, Nb, Ta, Cr and Ce, $X^2$ is at least one of Cu, Ni, Co, Fe, Mn and Zn, $X^3$ is at least one of Sb and Bi, $X^4$ is one or more alkali metals, $X^5$ is one or more alkaline earth metals, $X^6$ is at least one of Si, Al, Ti and Zr, a is from 1 to 6, b is from 0.2 to 4, c is from 0.5 to 18, d is from 0 to 40, e is from 0 to 2, f is from 0 to 4, g is from 0 to 40 and n is a number which is determined by the valency and frequency of the elements other than oxygen in IV.

18. The process according to claim 1, wherein the second fixed-bed catalyst has the following formula (V)

$Mo_{12}V_{a'}Y^1_{b'}Y^2_{c'}Y^5_{f'}Y^6_{g'}O_{n'}$ (V)

where $Y^1$ is at least one of W and Nb, $Y^2$ is at least one of Cu and Ni, $Y^5$ is at least one of Ca and Sr, $Y^6$ is at least one of Si and Al, a' is from 2 to 4, b' is from 1 to 1.5, c' is from 1 to 3, f' is from 0 to 0.5, g' is from 0 to 8 and n' is a number which is determined by the valency and frequency of the elements other than oxygen in V.

19. The process according to claim 1, wherein the second fixed-bed catalyst has the following formula (VI)

$[D]_p[E]_q$ (VI), where

D is $Mo_{12}V_{a''}Z^1_{b''}Z^2_{c''}Z^3_{d''}Z^4_{e''}Z^5_{f''}Z^6_{g''}O_{x''}$,

E is $Z^7_{12}Cu_{h''}H_{i''}O_{y''}$, $Z^1$ is at least one of W, Nb, Ta, Cr and Ce, $Z^2$ is at least one of Cu, Ni, Co, Fe, Mn and Zn, $Z^3$ is at least one of Sb and Bi, $Z^4$ is at least one of Li, Na, K, Rb, Cs and H, $Z^5$ is at least one of Mg, Ca, Sr and Ba, $Z^6$ is at least one of Si, Al, Ti and Zr, $Z^7$ is at least one of Mo, W, V, Nb and Ta, a" is from 1 to 8, b" is from 0.2 to 5, c" is from 0 to 23, d" is from 0 to 50, e" is from 0 to 2, f" is from 0 to 5, g" is from 0 to 50, h" is from 4 to 30, i" is from 0 to 20 and x" and y" are numbers which are determined by the valency and frequency of the elements other than oxygen in VI and p and q are numbers other than zero, whose ratio p/q is from 160:1 to 1:1.

20. The process according to claim 1, wherein the loading of the first fixed-bed catalyst is $\geq 250$ l (S.T.P.) of propene/l of catalyst bed·h.

21. The process according to claim 1, wherein the inert gas in reaction gas starting mixture 1 comprises ≧20% by volume of molecular nitrogen.

22. The process according to claim 21, wherein the inert gas in reaction gas starting mixture 1 comprises ≧95% by volume of molecular nitrogen.

23. The process according to claim 1, wherein the propene fraction of the reaction gas starting mixture 1 is from 4 to 15% by volume based on the total volume.

24. The process according to claim 23, wherein the propene fraction of the reaction gas starting mixture 1 is from 5 to 12% by volume based on the total volume.

25. The process according to claim 24, wherein the propene fraction of the reaction gas starting mixture 1 is from 5 to 8% by volume based on the total volume.

26. The process according to claim 1, wherein the volume ratio of propene to oxygen to inert gases including steam in the reaction gas starting mixture 1 is 1:(1.0 to 3.0):(5 to 25).

27. The process according to claim 26, wherein the volume ratio of propene to oxygen to inert gases including steam in the reaction gas starting mixture 1 is 1:(1.5 to 2.3):(10 to 15).

28. The process according to claim 1, wherein the molar $O_2$:acrolein ratio in the reaction gas starting mixture 2 is ≧0.5 and ≦3.

29. The process according to claim 28, wherein the molar $O_2$:acrolein ratio in the reaction gas starting mixture 2 is ≧1 and ≦2.

30. The process according to claim 29, wherein the molar $O_2$:acrolein ratio in the reaction gas starting mixture 2 is ≧1 and ≦1.5.

31. The process according to claim 1, wherein the volume ratio (1 (STP)) of acrolein to oxygen to steam to inert gas in the reaction gas starting mixture 2 is 1:(0.5 or 1 to 3):(0 to 20):(3 to 30).

32. The process according to claim 31, wherein the volume ratio (1 (STP)) of acrolein to oxygen to steam to inert gas in the reaction gas starting mixture 2 is 1:(1 to 3):(0.5 to 10):(7 to 10).

33. The process according to claim 1, wherein the loading of the second fixed-bed catalyst ≧250 l (S.T.P.) of acrolein/l of catalyst bed·h.

34. The process according to claim 1, wherein the inert gas in the reaction gas starting mixture 2 comprises ≧30% by volume of molecular nitrogen.

35. The process according to claim 34, wherein the inert gas in the reaction gas starting mixture 2 comprises ≧95% by volume of molecular nitrogen.

36. The process according to claim 1, wherein the inert gas in reaction gas starting mixture 2 comprises 5 to 20% by weight of $H_2O$ formed in the first reaction stage, and from 7 to 90% by weight of $N_2$.

37. The process according to claim 2, wherein the fixed-bed catalyst is unsupported.

38. The process according to claim 2, wherein the fixed-bed catalyst is coated.

39. The process according to claim 38, wherein the coated fixed-bed catalyst comprises support rings having a length of from 2 to 10 mm, an external diameter of from 2 to 10 mm and a wall thickness of from 1 to 4 mm.

40. The process according to claim 38, wherein the-coated fixed-bed catalyst comprises support rings having a length of from 3 to 6 mm, an external diameter of from 4 to 8 mm and a wall thickness of from 1 to 2 mm.

41. The process according to claim 38, wherein the coated fixed-bed catalyst comprises a catalytically-active oxide material having a thickness from 10 to 1,000 µm.

42. The process according to claim 38, wherein the coated fixed-bed catalysts are coated with a catalytically-active oxide having a thickness from 100 to 500 µm.

43. The process according to claim 38, wherein the fixed-bed catalyst is coated with a catalytically-active oxide material having a thickness from 150 to 250 µm.

44. The process according to claim 2, wherein the fixed-bed catalyst has the following formula (I)

$$Mo_{12}Bi_aFe_bX^1_cX^2_dX^3_eX^4_fO_n \qquad (I),$$

where $X^1$ is at least one of nickel and cobalt, $X^2$ is at least one of thallium, an alkali metal and an alkaline earth metal, $X^3$ is at least one of zinc, phosphorus, arsenic, boron, antimony, tin, cerium, lead and tungsten, $X^4$ is at least one of silicon, aluminum, titanium and zirconium, a is from 0.5 to 5, b is from 0.01 to 5, c is from 0 to 10, d is from 0 to 2, e is from 0 to 8, f is from 0 to 10 and n is a number which is determined by the valency and frequency of the elements other than oxygen in I.

45. The process according to claim 2, wherein the fixed-bed catalyst has the following formula (II)

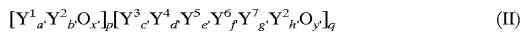

$$[Y^1_aY^2_bO_x]_p[Y^3_{c'}Y^4_{d'}Y^5_{e'}Y^6_{f'}Y^7_{g'}Y^2_{h'}O_{y'}]_q \qquad (II)$$

where $Y^1$ is at least one of bismuth, tellurium, antimony, tin and copper, $Y^2$ is at least one of molybdenum and tungsten, $Y^3$ is at least one of an alkali metal, thallium and samarium, $Y^4$ is at least one of an alkaline earth metal, nickel, cobalt, copper, manganese, zinc, tin, cadmium and mercury, $Y^5$ is at least one of iron, chromium, cerium and vanadium, $Y^6$ is at least one of phosphorus, arsenic, boron and antimony, $Y^7$ is at least one of a rare earth metal, titanium, zirconium, niobium, tantalum, rhenium, ruthenium, rhodium, silver, gold, aluminum, gallium, indium, silicon, germanium, lead, thorium and uranium, a' is from 0.01 to 8, b' is from 0.1 to 30, c' is from 0 to 4, d' is from 0 to 20, e' is from 0 to 20, f' is from 0 to 6, g' is from 0 to 15, h' is from 8 to 16, x' and y' are numbers which are determined by the valency and frequency of the elements other than oxygen in II and p and q are numbers whose ratio p/q is from 0.1 to 10.

46. The process according to claim 2, wherein the fixed-bed catalyst has the following formula (III)

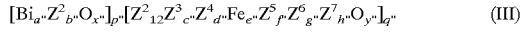

$$[Bi_{a''}Z^2_{b''}O_{x''}]_{p''}[Z^2_{12}Z^3_{c''}Z^4_{d''}Fe_{e''}Z^5_{f''}Z^6_{g''}Z^7_{h''}O_{y''}]_{q''} \qquad (III)$$

where
- $Z^2$ is at least one of molybdenum and tungsten,
- $Z^3$ is at least one of nickel and cobalt,
- $Z^4$ is at least one of thallium, an alkali metal and an alkaline earth metal,
- $Z^5$ is at least one of phosphorus, arsenic, boron, antimony, tin, cerium and lead,
- $Z^6$ is at least one of silicon, aluminum, titanium and zirconium,
- $Z^7$ is at least one of copper, silver and gold,
- a" is from 0.1 to 1,
- b" is from 0.2 to 2,
- c" is from 3 to 10,
- d" is from 0.02 to 2,
- e" is from 0.01 to 5,
- f" is from 0 to 5,
- g" is from 0 to 10,
- h" is from 0 to 1,
- x" and y" are numbers which are determined by the valency and frequency of the elements other than oxygen in III and
- p" and q" are numbers whose ratio p"/q" is from 0.5 to 2.

47. The process according to claim 2, wherein the loading of the fixed-bed catalyst is $\geq 250$ l (S.T.P.) of propene/l of catalyst bed·h.

48. The process according to claim 2, wherein the inert gas in reaction gas starting mixture 1 comprises $\geq 20\%$ by volume of molecular nitrogen.

49. The process according to claim 48, wherein the inert gas in reaction gas starting mixture 1 comprises $\geq 95\%$ by volume of molecular nitrogen.

50. The process according to claim 2, wherein the propene fraction of the reaction gas starting mixture 1 is from 4 to 15% by volume based on the total volume.

51. The process according to claim 50, wherein the propene fraction of the reaction gas starting mixture 1 is from 5 to 12% by volume based on the total volume.

52. The process according to claim 51, wherein the propene fraction of the reaction gas starting mixture 1 is from 5 to 8% by volume based on the total volume.

53. The process according to claim 2, wherein the volume ratio of propene to oxygen to inert gases including steam in the reaction gas starting mixture 1 is 1:(1.0 to 3.0):(5 to 25).

54. The process according to claim 53, wherein the volume ratio of propene to oxygen to inert gases including steam in the reaction gas starting mixture 1 is 1:(1.5 to 2.3):(10 to 15).

55. The process according to claim 2, wherein the molar $O_2$:acrolein ratio in the reaction gas starting mixture 2 is $\geq 0.5$ and $\leq 3$.

56. The process according to claim 56, wherein the molar $O_2$:acrolein ratio in the reaction gas starting mixture 2 is $\geq 1$ and $\leq 2$.

57. The process according to claim 56, wherein the molar $O_2$:acrolein ratio in the reaction gas starting mixture 2 is $\geq 1$ and $\leq 1.5$.

* * * * *